(12) United States Patent
Barry et al.

(10) Patent No.: US 7,699,804 B2
(45) Date of Patent: Apr. 20, 2010

(54) FLUID EJECTION SYSTEM

(75) Inventors: James J. Barry, Hanover, NH (US);
Mark C. Bagley, Grafton, NH (US);
Peter L. Burghardt, Wilmot, NH (US);
Steven J. Fulton, Enfield, NH (US)

(73) Assignee: Creare Inc., Hanover, NH (US)

( * ) Notice: Subject to any disclaimer, the term of this patent is extended or adjusted under 35 U.S.C. 154(b) by 1278 days.

(21) Appl. No.: 10/768,854

(22) Filed: Jan. 30, 2004

(65) Prior Publication Data

US 2004/0186432 A1 Sep. 23, 2004

Related U.S. Application Data

(60) Provisional application No. 60/444,290, filed on Jan. 31, 2003.

(51) Int. Cl.
*A61M 37/00* (2006.01)

(52) U.S. Cl. .............. 604/89; 604/90; 604/91; 604/152; 604/247; 604/256

(58) Field of Classification Search .......... 604/68, 604/152, 247, 249, 256, 523, 533, 534, 89–91
See application file for complete search history.

(56) References Cited

U.S. PATENT DOCUMENTS

| | | | |
|---|---|---|---|
| 337,707 A | 3/1886 | Siegenthaler et al. | |
| 441,238 A | 11/1890 | Guptill | |
| 857,739 A | 6/1907 | Kennerly et al. | |
| 1,456,469 A | 5/1923 | Schwidetzky | |
| 1,998,692 A | 4/1935 | Van Rossem et al. | 259/113 |
| 2,541,621 A | 2/1951 | Thompson | 128/218 |
| 3,052,240 A | 9/1962 | Silver et al. | 128/218 |
| 3,140,078 A | 7/1964 | Krahe et al. | 259/47 |
| 3,164,303 A | 1/1965 | Trautmann | 222/190 |

(Continued)

FOREIGN PATENT DOCUMENTS

EP 89101509.1 1/1989

(Continued)

OTHER PUBLICATIONS

LectraJet HS High Speed Jet Injection System for Mass Immunization Campaigns; Centers for Disease Control and Prevention, Atlanta, GA; http://www.dantonioconsultants.com/prod_ji_human.htm.

*Primary Examiner*—Nicholas D Lucchesi
*Assistant Examiner*—Laura A Bouchelle
(74) *Attorney, Agent, or Firm*—Downs Rachlin Martin PLLC

(57) ABSTRACT

A fluid ejection system (20) comprising a cartridge (24), an ejector (32, 300) and, optionally, a fill station (28) for filling the cartridge with a fluid, such as a vaccine. In some embodiments (52), the cartridge includes a transfer passageway (96) for receiving fluid from the fill station. In other embodiments (200, 400), the cartridge includes a vented fluid reservoir (208, 408) offset from an ejection chamber (224, 420). In yet other embodiments (500, 600), the cartridge includes a vented fluid reservoir chamber (512, 636) inline with the ejection chamber (508, 644). In still other embodiments (700, 1000, 1100), the cartridge includes first and second chambers (728, 736, 1036, 1048, 1136, 1148) initially fluidly sealed from on another by a valve, e.g., either a traveling valve (704, 800, 900, 1200, 1300) or a temporarily stationary valve (1004, 1104).

24 Claims, 18 Drawing Sheets

U.S. PATENT DOCUMENTS

| | | | |
|---|---|---|---|
| 3,814,941 A | 6/1974 | Czaplinski | 250/430 |
| 4,449,645 A * | 5/1984 | Korwin et al. | 222/49 |
| 4,698,055 A | 10/1987 | Sealfon | 604/82 |
| 4,861,335 A * | 8/1989 | Reynolds | 604/88 |
| 5,080,649 A | 1/1992 | Vetter | 604/91 |
| 5,599,312 A * | 2/1997 | Higashikawa | 604/191 |
| 5,630,800 A * | 5/1997 | Blank et al. | 604/82 |
| 6,010,485 A | 1/2000 | Buch-Rasmussen et al. | 604/191 |
| 6,610,042 B2 | 8/2003 | Leon et al. | 604/500 |
| 2002/0165496 A1 | 11/2002 | Thompson | 604/181 |
| 2003/0050610 A1 * | 3/2003 | Newton et al. | 604/256 |

FOREIGN PATENT DOCUMENTS

| | | |
|---|---|---|
| GB | 1595204 | 7/1977 |

* cited by examiner

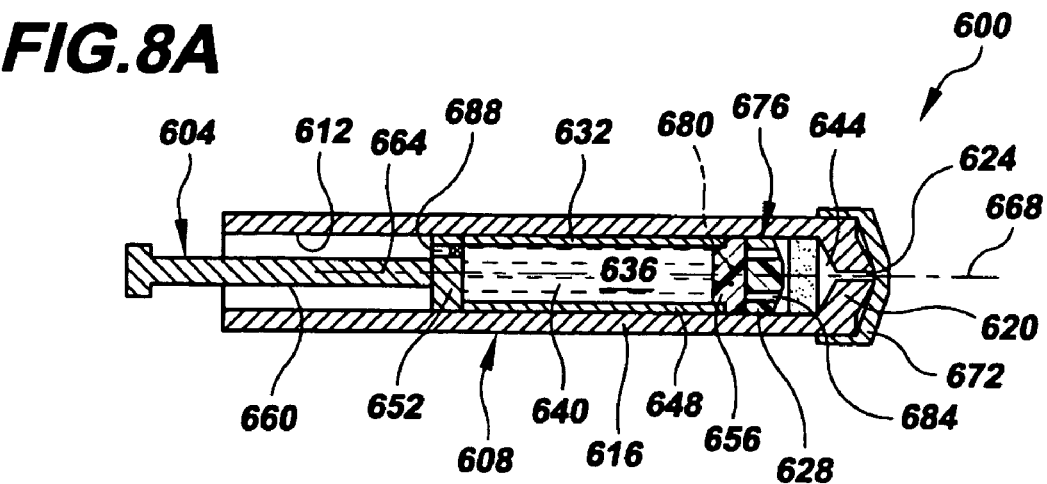
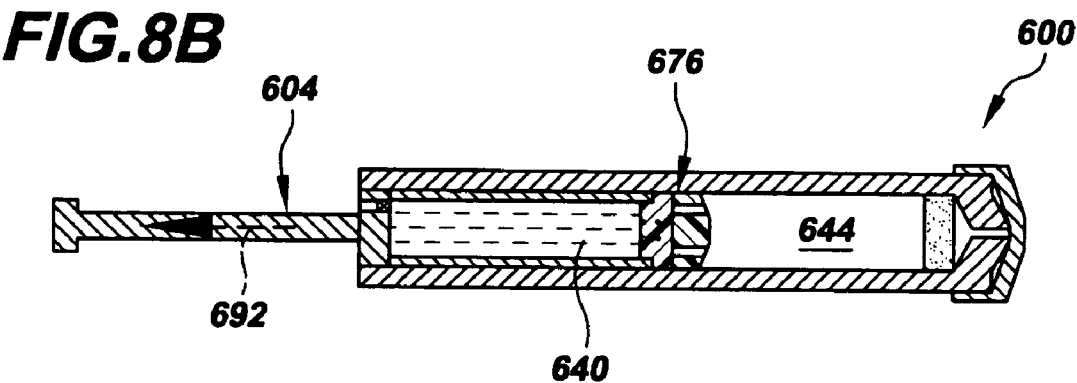
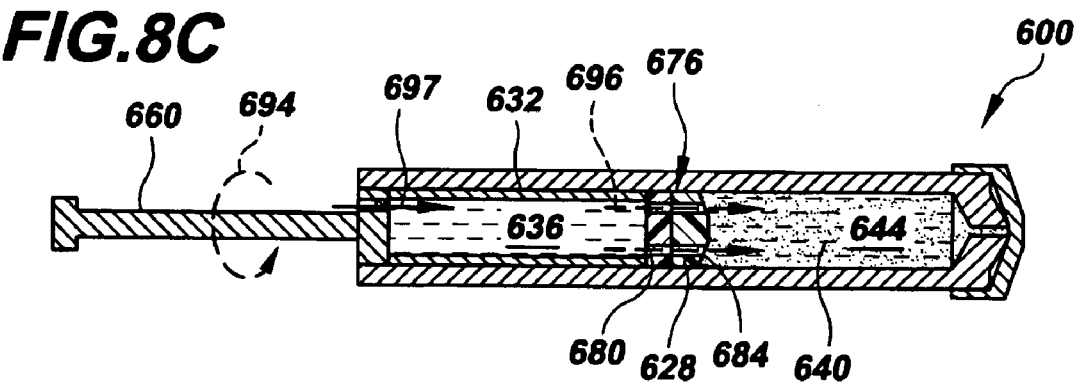
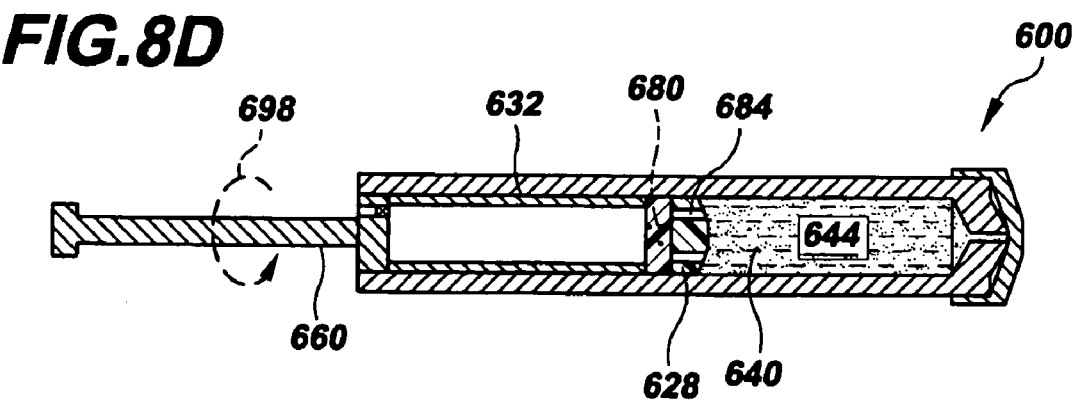

FLUID EJECTION SYSTEM

RELATED APPLICATION DATA

This application claims the benefit of priority of U.S. Provisional Patent Application Ser. No. 60/444,290, filed Jan. 31, 2003, and titled "Jet Injector Cartridges," that is incorporated by reference herein in its entirety.

FIELD OF THE INVENTION

The present invention generally relates to the field of fluid delivery systems. In particular, the present invention is directed to a fluid ejection system.

BACKGROUND OF THE INVENTION

Vaccination of humans and animals against various diseases has been, and continues to be, an important component of controlling the spread of these diseases. For example, measles remains a critical public health issue for humans, resulting in over one million deaths per year globally. Vaccination against measles is one of the most cost-effective public health measures available to control the spread of measles, and global eradication of the disease is technically feasible using current vaccinations. A global eradication campaign is presently under consideration by the World Health Organization. Unlike past and ongoing eradication campaigns for smallpox and polio, however, a simple and low-cost vaccine administration technique is not presently available for measles. Current practice remains injection using a hypodermic syringe.

Hypodermic syringe methods of vaccination have numerous drawbacks, including the need for skilled personnel, risk of blood-borne disease, high cost, patient aversion to injection and the need to safely dispose of large quantities of needles and syringes. For a measles eradication campaign on a global scale, use of conventional needles and syringes is generally considered impractical. Streamlined techniques utilizing alternatives to hypodermic syringes, such as jet injectors, are necessary for safe and cost-effective mass vaccination campaigns.

Another issue regarding measles vaccination lies in reconstituting the vaccine. Current vaccine administration techniques require reconstitution of the vaccine by drawing a sterile diluent from a sealed vial via needle and syringe and injecting the diluent into another sealed vial containing lyophilized vaccine. The vial containing the diluent and lyophilate is then shaken to mix the diluent and lyophilate and complete the reconstitution. Thus, even if needle-free administration of the vaccine is subsequently used, the reconstitution process requires the use of needles and syringes, providing an opportunity for contamination of the reconstituted vaccine by reuse of dirty diluent-injection needles, the need to dispose of used diluent needles and syringes, a chance for use of the wrong diluent, occasion for measurement errors in obtaining proper dilution and the possibility of needle stick injuries by less-skilled, fatigued or distracted personnel. Moreover, the use of separate supply vials for vaccine and diluent requires multiple sterile containers to be ordered, transported, inventoried, coordinated and monitored.

Jet injection of vaccines was used successfully for many years until concerns regarding patient-to-patient contamination from multiple use injectors arose in the late 1980s and early 1990s. Substantial efforts are now underway to develop new injectors that utilize disposable fluid pathways to prevent contamination. Typically, these disposable pathways are in the form of cartridges that are similar in shape and functions to a conventional hypodermic syringe having a generally cylindrical barrel, or housing, and a plunger. Rapid movement of the plunger in the housing toward an orifice generates high pressures, and a jet of high-velocity liquid issues from the orifice and pierces the skin of a patient.

What is needed is an ejection system that may be used for, among other things, administering vaccines while reducing or eliminating the drawbacks of conventional vaccination systems, including the vaccination systems discussed above.

SUMMARY OF THE INVENTION

In one aspect, the present invention is directed to an ejector for ejecting a fluid from a syringe. The syringe includes a cavity, a retractable structure extending within the cavity, a piston located within the cavity and an outlet in fluid communication with the cavity. The ejector comprises a receiver operatively configured to receive the syringe. A first mechanism engages the retractable structure when the syringe is engaged with the receiver and is operatively configured to move the retractable in a direction away from the outlet. A second mechanism is operatively configured to move the piston in a direction toward the outlet when the syringe is engaged with the receiver so as to eject the fluid via the outlet from a portion of the cavity located between the piston and the outlet.

In another aspect, the present invention is directed to a method of ejecting a fluid from a syringe. The syringe includes a chamber having a longitudinal central axis, a piston slidable within the chamber along the longitudinal central axis, an outlet in fluid communication with the chamber and a retractable structure extending into the chamber. The method comprises the step of first engaging the syringe with an ejector having a first mechanism operatively configured to move the retractable structure in a direction away from the outlet so that the retractable structure is engaged with the first mechanism. Then, the first mechanism is actuated so as to retract the retractable structure. Then, the fluid is provided to a portion of the chamber located between the piston and the outlet.

In yet another aspect, the present invention is directed to a syringe comprising a housing defining a chamber having a longitudinal central axis. A piston is slidable within the chamber along the longitudinal central axis. An outlet is in fluid communication with the chamber and extends through the housing. A transfer passageway extends through the housing and spaced from the outlet and the longitudinal central axis. A transfer passageway seal removably seals the transfer passageway. The transfer passageway seal is removable by moving the piston.

In a further aspect, the present invention is directed to a syringe comprising a housing defining a chamber having a first longitudinal central axis and a reservoir having a second longitudinal central axis substantially collinear with the first longitudinal central axis. A valve is located between the chamber and the reservoir. A piston is spaced from the valve along the second longitudinal axis. An actuator is coupled to the valve so that the valve is opened by moving the actuator and at least a portion of the valve is moved generally along the second longitudinal central axis by the actuator when the actuator is moved.

These and other aspects of the present invention are addressed below.

BRIEF DESCRIPTION OF THE DRAWINGS

For the purpose of illustrating the invention, the drawings show forms of the invention that are presently preferred. However, it should be understood that the present invention is not limited to the precise arrangements and instrumentalities shown in the drawings, wherein:

FIGS. 8A-8E are cross-sectional views of an alternative vented inline-reservoir cartridge of the present invention, illustrating its operation;

DETAILED DESCRIPTION OF THE DRAWINGS

Figure 1:
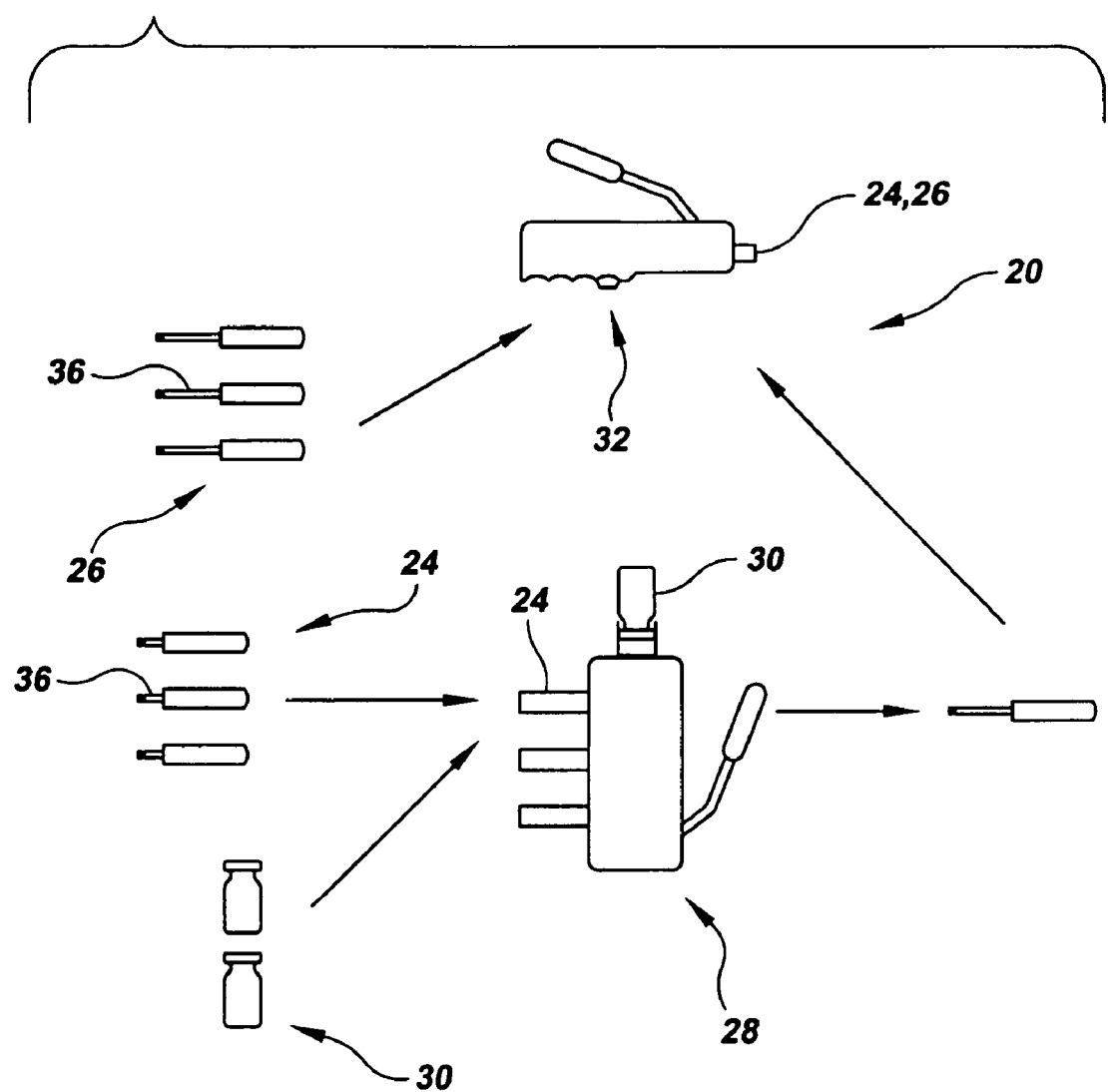
FIG. 1 is a partial schematic of a fluid ejection system of the present invention.

Referring now to the drawings, FIG. 1 shows in accordance with the present invention a fluid ejection system, which is generally denoted by the numeral 20. Fluid ejection system 20 may be used for any number of applications in which it is desired to eject a fluid (not shown) from one or more containers, such as cartridges 24, 26. One application, of course, is the delivery of vaccine, such as a measles vaccine, to patients (not shown). In this application, fluid ejection system 20 may be more conventionally termed "fluid injection system" since in a vaccination application, the vaccine is injected into a patient. It is noted that the terms "ejection" and "injection" (and similar terms) are selected based on a frame of reference. That is, system 20 is an ejection system relative to cartridges 24, since fluid is ejected out of the cartridges during use. On the other hand, system 20 is an injection system relative to a patient or other body because, in this case, fluid from each cartridge 24 is injected into that patient or body. As used herein and in the claims appended hereto, unless noted otherwise the frame of reference will be with respect to each cartridge 24, or its equivalent. Therefore, unless noted otherwise, the term "ejection," "ejector" and similar terms will be used, although "injection," "injector" and similar terms may also be appropriate.

Although fluid ejection system 20 is particularly useful in the context of vaccination, those skilled in the art will readily recognize that there are many applications for this system, including the delivery of medications and fluids other than vaccines, such as paints, flavorings, additives, reagents, adhesives, sealants and lubricants, among many others. Due to such ready recognition, it is not necessary, nor practical, to list all suitable applications for fluid ejection system 20. In this connection, it is noted that as used herein and in the appended claims, the term "fluid" is used in its broadest sense to mean a substance that exists or is held to exist as a continuum marked by low resistance to flow and the tendency to assume the shape of its container. Accordingly, liquids, liquid suspensions, flowable particular solids, gases, and aerosols are included in the intended meaning of "fluid." In the case of the measles vaccination application discussed above in the Background section hereof, the term "fluid" can be used to describe both the liquid diluent used to reconstitute the vaccine and the reconstituted vaccine, which consists of the diluent and the lyophilized vaccine [lyophilized vaccine contains both virus and excipients].

In general, cartridges 24 may be characterized as either "unfilled" or "partially pre-filled," depending upon the material(s) the cartridges contain. That is, if cartridges 24 do not contain any material(s) to be ejected, they may be considered "unfilled" cartridges. If cartridges contain only some, but not all, of the material(s) to be ejected, they may be considered "partially pre-filled" cartridges. When cartridges 24 are either partially-pre-filled or unfilled, they must first be charged with the absent material(s) prior to ejection.

Consequently, fluid ejection system 20 may include a fill station 28 for providing a fluid to each cartridge from one or more reservoirs 30. To illustrate the case of partially-filled cartridges 24 using the measles vaccination application, each cartridge may be initially charged with only the lyophilized vaccine, such that a later addition of a diluent reconstitutes the measles vaccine. In this case, fill station 28 may be used to add the diluent to each cartridge 24 for reconstituting the vaccine. In contrast, in the case wherein cartridges 24 are initially unfilled, fill station 28 may be used to charge each cartridge with the necessary amount of fluid to be ejected from that cartridge. In the context of the measles vaccine application, fill station 28 may be used to charge each cartridge with a previously-reconstituted vaccine. Since the applications of fluid ejection system 20 are numerous and readily discernable, it is not necessary to exhaustively list alternatives.

It is noted that although fill station 28 has been described in connection with cartridges 24, it is not so limited. Rather, fill station 28 may be used to fill other working cylinder devices, which are referred to herein and in the appended claims as "syringes," as applied in a broad sense. In the present context, the term "syringe" shall mean a device that includes a barrel, housing or similar structure that defines a cavity, chamber, or similar structure in which a piston, plunger or similar structure is slidable so as to eject a fluid there. It is intended that the term "syringe" include, among other things, cartridges, medical syringes, e.g., hypodermic syringes, and similarly-structured working cylinders. Accordingly, fill station 28 may be adapted to charge any sort of syringe with a fluid.

On the other hand, cartridges 26 may be considered "prefilled" cartridges in that they contain all of the material(s) to be ejected. That said, it is noted that although cartridges 26 are pre-filled, this does not necessarily mean that the material(s) are ready to be ejected. In the case of cartridges 26 for ejecting, e.g., two or more materials, it may be necessary to mix the materials with one another prior to ejection. For example, each cartridge 26 may have separate compartments for storing the two or more materials. Various pre-filled cartridges of this type are described below.

Fluid ejection system 20 may also include an ejector 32 for ejecting the fluid from each cartridge 24 and/or each cartridge 26. If a cartridge 24, 26 is ejection-ready prior to being engaged with ejector 32, i.e., the cartridge is pre-filled and pre-mixed or filled at filling station 30, the ejector may be a conventional, or similar, "one-way-action" ejector. Generally, "one-way-action" in this context means that ejector 32 has one primary function of ejecting fluid from each cartridge, e.g., by depressing a plunger 36 of cartridge 24, 26. In the context of measles vaccination, a suitable one-way-action ejector is the LectraJet HS® high speed jet injector available from D'Antonio Consultants International, Inc., East Syracuse, N.Y. Of course, ejector 32 need not be a high speed ejector, depending upon the application.

If, on the other hand, a cartridge 24 is not filled, or is pre-filled, but unmixed, prior to being engaged with ejector 32, e.g., the cartridge is partially filled, unfilled or has an internal valve (see FIGS. 4A-4D and FIG. 6 et seq.) that requires actuation in order to mix two substances (e.g., a diluent and lyophilate) stored in separate compartments until just prior to ejection, the ejector may be a "two-way-action" ejector. In this context, "two-way-action" generally means that ejector 32 has two primary functions. One primary function is to either move plunger 36 so as to effect charging from a reservoir in fluid communication with the corresponding cartridge 24 or moving a valve actuator (see, e.g., valve actuator 756 of FIGS. 9A and 9B) that actuates a valve (704 in FIGS. 9A and 9B) so as to effect mixing of two or more materials, e.g., a diluent and a lyophilate, among many others. The other primary function is to eject fluid from cartridge 24. Cartridges 24, 26, fill station 28 and a two-way-action embodiment of ejector 32 are described below in greater detail.

Figure 2A:
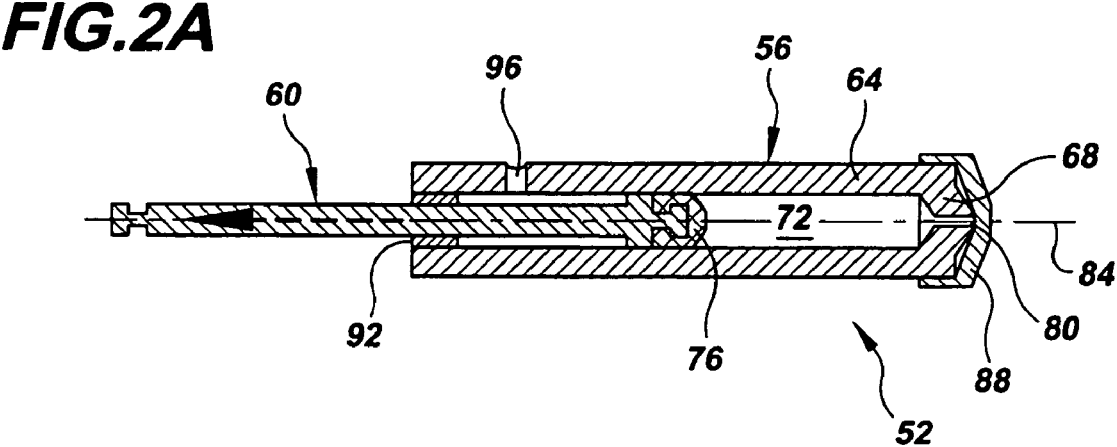
FIG. 2A is a cross-sectional view of a cartridge that may be used with the fluid ejection system of FIG. 1.

FIG. 2A shows a cartridge 52 that may be used for cartridges 24 of fluid ejection system 20 of FIG. 1. Cartridge 52 generally includes a housing 56 and a plunger 60. Housing 56 may include a sidewall 64 and an end wall 68 that cooperate to substantially define a chamber 72 for containing a fluid (not shown) to be ejected from cartridge 52. Housing 56 may be made of any suitable material, such as plastic, glass, metal, e.g., stainless steel, among others. Plunger 60 may include a piston 76 located in chamber 72 and slidably sealingly engaged with sidewall 64 of housing 56. Each of plunger 60 and piston 76 may be made of a suitable material. For example, plunger 60 may be made of plastic or metal, among others, and piston 76 may be made of plastic, rubber or other suitable material. Depending upon the design of piston 76, one or more O-rings or similar structures may be used to effect a fluid seal between the piston and sidewall 64 of housing 56. The functions of plunger 60 are described below.

Cartridge 52 further includes an outlet 80 for passing the fluid from chamber 72 out of the cartridge. Outlet 80 may be defined by any of a variety of structures, such as a high-speed nozzle or a low speed nozzle, or a passageway for connecting with an external passageway, such as a hypodermic needle or tubing, among other things. Outlet 80 may be located anywhere desired, such as in end wall 68 along the longitudinal central axis 84 of chamber 72 as shown, or otherwise, such as off-center relative to the longitudinal central axis, either on sidewall 64 or end wall 68. Outlet 80 may be sealed with a suitable outlet seal, such as cap 88 shown, plug or frangible seal, among others. If cap 88 is provided, it may be of any suitable type, such as press-fit or threaded, among others.

Cartridge 52 may also includes a plunger seal 92 that provides a seal between plunger 60 and sidewall 64, e.g., to inhibit contamination from entering chamber 72. A transfer passageway 96 may be provided to housing 56, e.g., in sidewall 64, that allows cartridge 52 to be filled with a fluid. When empty, cartridge 52 may be charged with fluid, e.g., using either fill station 28 or a two-way-action embodiment of ejector 32 of FIG. 1. Generally, cartridge 52 may be charged as follows when the starting position of piston 76 is proximate end wall 68, and cap 88 is present. First, transfer passageway 96 is placed in fluid communication with a fluid delivery system (not shown) that will provide a fluid to cartridge 52.

Once transfer passageway 96 is in fluid communication with a fluid delivery system, plunger 60 may be retracted so as to cause a vacuum to form within chamber 72 between end wall 68 and piston 76. Once piston 76 moves past transfer passageway 96, the vacuum within chamber 72 will draw fluid from the fluid delivery system into the chamber. Cap 88 may then be removed. At this point, cartridge 52 is generally ready for ejecting fluid from chamber 72. Accordingly, plunger 60 may be pushed toward end wall 68 so as to eject the fluid from chamber 72.

Figure 2B:
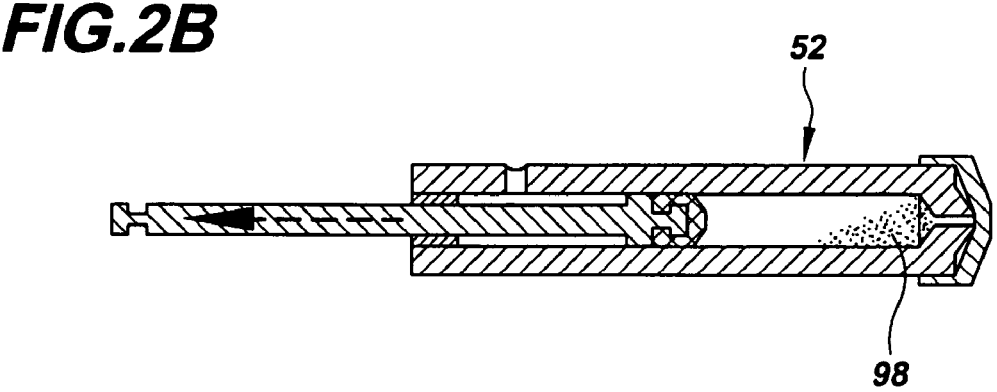
FIG. 2B shows the same cartridge pre-charged with a material.

FIG. 2B shows cartridge 52 of FIG. 2A pre-charged with a material 98 that will generally be mixed with a fluid when chamber 72 is filled as discussed immediately above. Material 98 may be any material that may be mixed with a fluid. In this connection, material 98 may be a powder or other particulate, a gas, a liquid, a dissolvable solid or gel, or any combination of these, among others. For example, in the context of measles vaccination, material 98 may be lyophilized vaccine.

Figure 3:
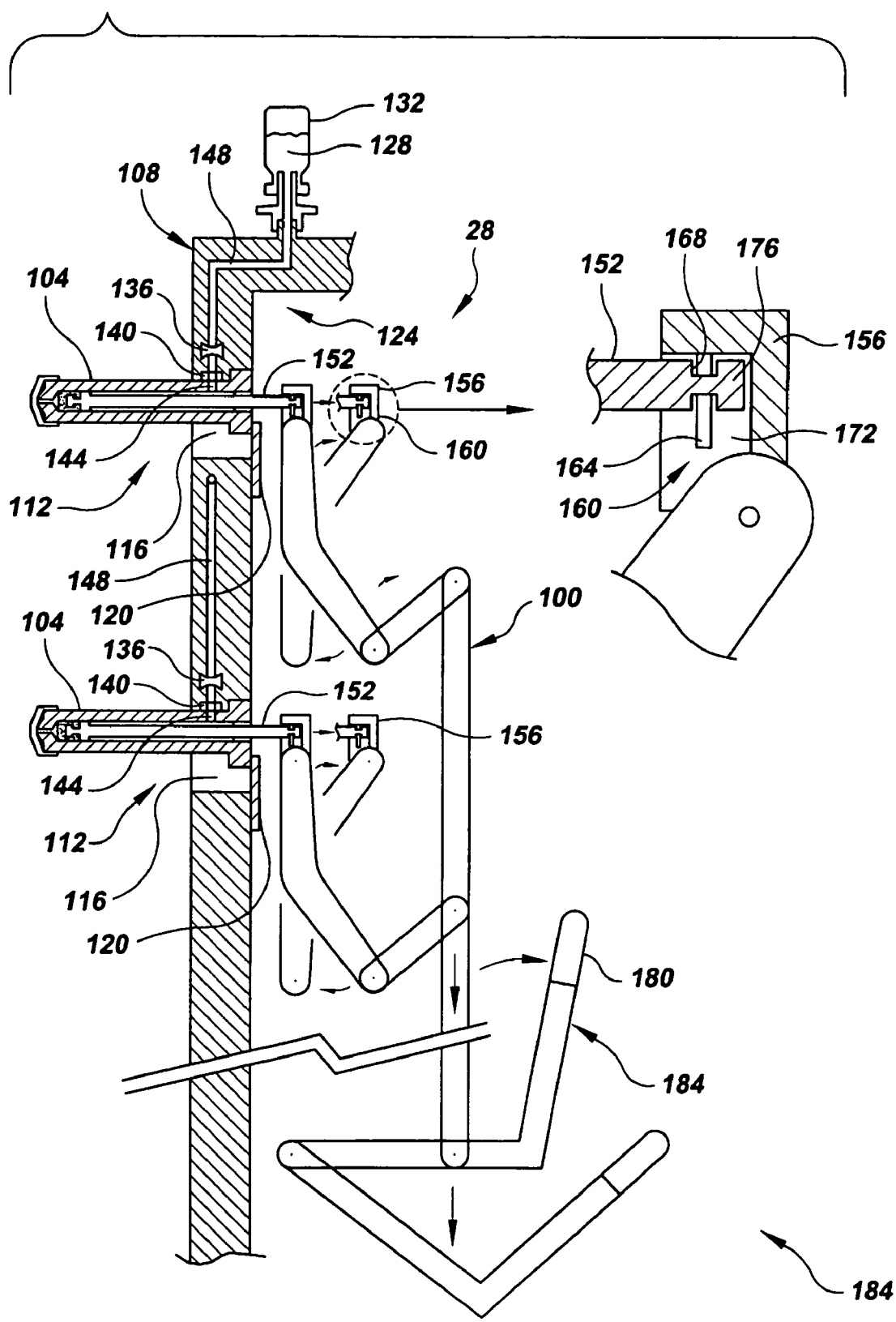
FIG. 3 is a cross-sectional view of a fill station that may be used with the fluid ejection system of FIG. 1.

FIG. 3 illustrates an exemplary fill mechanism 100 that may be used for fill station 28 of fluid ejection system 20 of FIG. 1 for filling one or more cartridges 104, e.g., of the type shown in FIGS. 2A and 2B. Fill station 28 may include a housing 108 and one or more receivers 112 each for receiving a cartridge 104. Each receiver 112 may include a holder, e.g., a spring clip 116, for holding a corresponding cartridge 104 properly within that receiver. With spring clip 116 shown, cartridge 104 may be properly engaged with receiver 112 by first inserting the plunger end of the cartridge until housing 108 contacts a stop 120, and then lifting the cartridge upward to engage the spring clip.

Fill station 28 may further include a fluid delivery system 124 for delivering to each cartridge 104 properly engaged with one of receivers 112, fluid 128 from a reservoir 132, e.g., a vaccine vial or other container containing enough fluid for filling more than one cartridge. Fluid delivery system 124 may include a valve 136 and/or seal 140 for engaging transfer passageway 144 of each properly engaged cartridge 104 and a fluid pathway 148 connecting reservoir 132 to each valve 136 or seal 140. Fluid pathway 148 may comprise tubing, passageways in housing 108 or another part of fill station 28, or other type of conduit. Each seal 140 may be provided for forming a fluid seal with the exterior of a corresponding cartridge 104 around the respective transfer passageway 144. Seal 140 may be made of a suitable material, such as an elastomer.

Each valve 136 may be provided to allow the corresponding fluid pathway 148 to be closed, at least while the respective cartridge 104 is not properly engaged within that receiver 112. Each valve 136 may be actuated by a cartridge 104 when that cartridge is engaged with the corresponding receiver 112, or may be actuated by another means (not shown), such as an automatic actuator or a manual actuator. Those skilled in the art will appreciate that a large variety of valves and valve actuators may be adapted for use with fill station 28, such that an exhaustive list is not necessary for those skilled in the art to appreciate the broad scope of the invention.

Fill mechanism 100 may be any suitable manual or automatic mechanism for retracting each plunger 152 of the cartridge(s) 104 properly engaged with fill station 28. Mechanism 100 may be a purely mechanical link-type system as shown or may alternatively include, with or without mechanical linkages, one or more actuators, such as motors, hydraulic or pneumatic, among others. Those skilled in the art will readily appreciate the variety of mechanisms 100 that may be implemented in fill station 28 for retracting plunger(s) 152. Fill mechanism 100 may include a socket 156 corresponding to each receiver 112 for engaging a corresponding plunger 152 in order to retract that plunger. For example, each socket 156 may include a recessed channel/slot receiver 160, wherein the slot 164 engages an annular recess 168 in plunger 152 and the channel 172 engages a head 176 of the plunger when cartridge 104 is moved upward to engage spring clip 116. Of course, another type of means for gripping/engaging plunger 152 may be used.

If fill mechanism 100 is manually operated, it may include a handle 180 for a user to grasp and move so as to fill cartridges 104. In the case of fill mechanism 100 shown, once one or more cartridges 104 are properly engaged with fill station 28 as described above, the appropriate instances of valves 136 are opened and these cartridges are filled by a user pulling handle 180 generally in a clockwise direction (relative to FIG. 3). This causes mechanism 100 to retract the corresponding plunger(s) 152 so as to create a vacuum in each cartridge 104. As described above in connection with FIG. 2A, once each plunger 152 is retracted sufficiently, fluid 128 will be drawn from reservoir 132 via the respective fluid pathway 148 into the corresponding cartridge 104. Once each cartridge 104 has been properly charged, it may then be removed from fill station 28 by disengaging it from spring clip 116 and moving it away from the fill station. Once all cartridges 104 have been removed from fill station 28, the user may return handle 180 to its receiving position 184 by moving it generally counterclockwise. At this point, fill station 28 is generally ready to be reloaded with one or more cartridges 104. However, reservoir 132 may need to be replaced or refilled if an insufficient amount of fluid 128 for performing another fill cycle remains in the reservoir.

Figure 4A:
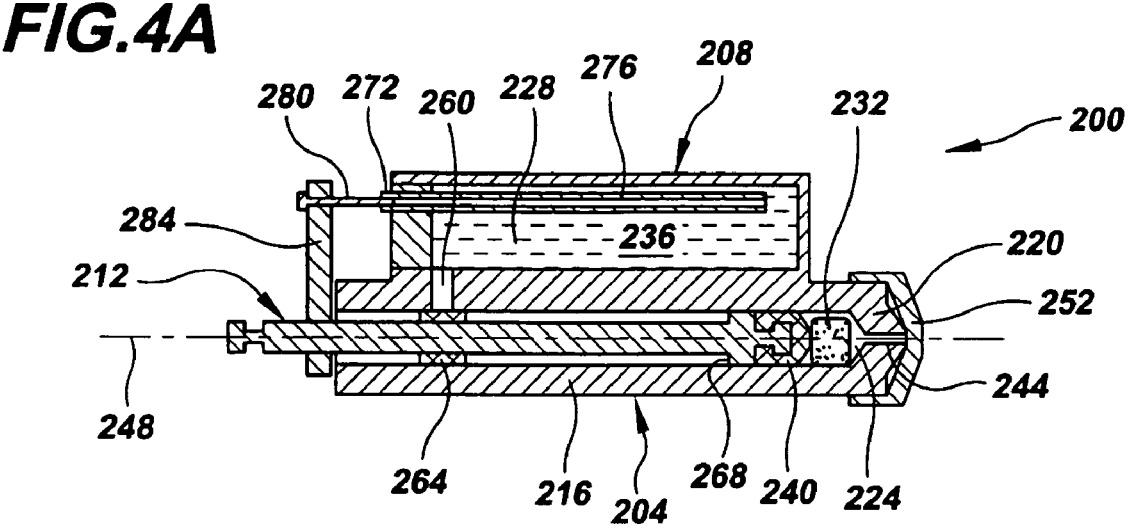
FIGS. 4A-4D are cross-sectional views of an offset-reservoir cartridge of the present invention, illustrating its operation.

FIGS. 4A-4D show an alternative cartridge 200 that may be used as cartridge 24 of fluid ejection system 20 of FIG. 1. Referring first to FIG. 4A, cartridge 200 may generally comprise a housing 204, a reservoir 208 and a plunger 212. Housing 204 may include a sidewall 216 and end wall 220 that cooperate to substantially define an ejection chamber 224 for containing a fluid 228 (contained in reservoir 208 in FIG. 4A) to be ejected from cartridge 200. As with cartridge 52 as shown in FIG. 2B, ejection chamber 224 may optionally contain a material 232, e.g., a lyophilate, to be mixed with fluid 228 during charging of this chamber with fluid. Reservoir 208 generally defines a reservoir chamber 236 for containing fluid 228 that will eventually be ejected from cartridge 200. Reservoir 208 may be integral with housing 204 or formed separately from the housing and attached thereto. Housing 204 and reservoir 208 may be made of any suitable material, such as plastic, glass, or metal, e.g., stainless steel, among others. Plunger 212 may include a piston 240 located in ejection chamber 224 and slidably sealingly engaged with housing 204. Each of plunger 212 and piston 240 may be made of a suitable material. For example, plunger 212 may be made of plastic or metal, among others, and piston 240 may be made of plastic, rubber, or other suitable material. Depending upon the design of piston 240, the piston may include one or more O-rings (not shown) or similar structures for effecting a fluid seal between the piston and housing 204.

Cartridge 200 may further include an outlet 244 for passing fluid 228 from ejection chamber 224 out of the cartridge. Outlet 244 may be defined by any of a variety of structures, such as a high-speed nozzle, a low speed nozzle, or a passageway for connecting with one or more external passageways, such as a hypodermic needle or tubing, among others. Outlet 244 may be located anywhere desired, such as along longitudinal central axis 248 of ejection chamber 224 as shown, or otherwise, such as off-center relative to the longitudinal central axis, either on sidewall 216 or end wall 220. Outlet 244 may be sealed with a suitable outlet seal, such as cap 252 shown, plug or frangible seal, among others. If cap 252 is provided, it may be of any suitable type, such as press-fit or threaded, among others.

One or more transfer passageways 260 extend between reservoir chamber 236 and ejection chamber 224, e.g., in sidewall 216, to allow ejection chamber 224 to be charged with fluid 228 from reservoir chamber 236 at an appropriate time. Prior to ejection chamber 224 of housing 204 being charged with fluid 228 from reservoir 208, transfer passageway 260 may be sealed with a suitable transfer passageway seal 264 that provides a valve to inhibit the fluid from flowing from reservoir chamber 236 to ejection chamber 224 at an inappropriate time. Transfer passageway seal 264 may be any suitable type of seal, such as the sliding seal shown, or a frangible seal, among others. In addition, transfer passageway seal 264 may be actuated by the movement of plunger 212. In the embodiment shown, sliding transfer passageway seal 264 is moved by plunger 212 upon retraction of the plunger from ejection chamber 224 via contact with a shoulder 268 on the plunger.

In order to facilitate the charging of ejection chamber 224, reservoir 208 may include a vent 272 for allowing atmospheric air or other fluid (not shown) to displace fluid 228 within reservoir chamber 236 as ejection chamber 224 is being charged. Vent 272 may be located at any suitable location, such as at the "rear" of reservoir 208. Depending generally upon the location of vent 272, reservoir 208 may optionally include a vent tube 276 within reservoir chamber 236 to inhibit the air or other fluid from entering ejection chamber 224 as fluid 228 is being drawn into the chamber from reservoir 208. In the embodiment shown, vent tube 276 extends to a location proximate "front" of reservoir 208, distal from transfer passageway 260. When cartridge 200 is not being used, vent 272 is sealed with a vent seal 280, which may be mechanically coupled with plunger 212, e.g., by linkage 284, so as to be moved out of sealing engagement with vent 272 when the plunger is moved appropriately. In the embodiment shown, vent seal 280 is disengaged from vent 272 upon retraction of plunger 212 within ejection chamber 224. Vent seal 280 may be made of any material, e.g., plastic or rubber, among others, that provides the desired seal. Linkage 284 may be relatively rigid or flexible and comprise more than one member, if desired.

Figure 4B:
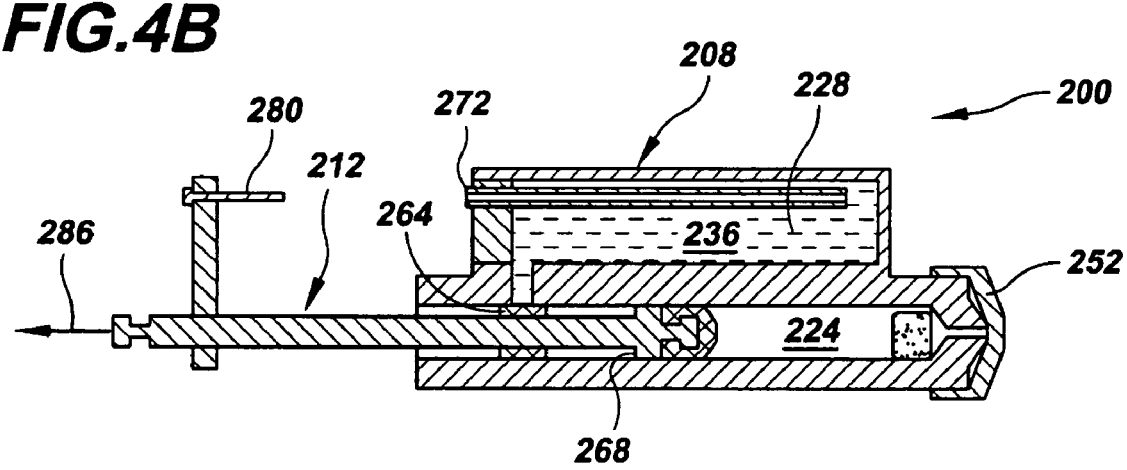

Generally, cartridge 200 may be used as follows. An initial state of cartridge 200 is shown in FIG. 4A. In this initial state, fluid 228 is contained within reservoir chamber 236, plunger 212 is inserted in ejection chamber 224 so that piston 240 is proximate end wall 220, transfer passageway seal 264 is sealing transfer passageway 260, cap 252 is sealing outlet 244 and vent seal 280 is sealing vent 276. As mentioned above, material 232 may optionally be present within ejection chamber 224. To charge ejection chamber 224 with fluid 228 from reservoir chamber 236, as shown in FIG. 4B plunger 212 is retracted within the ejection chamber (as indicated by arrow 286), e.g., manually or using ejector 32 of FIG. 1, with cap 252 in place so as to create a vacuum in the ejection chamber. As a result of plunger 212 being retracted, vent seal 280 is disengaged from vent 272 of reservoir 208, so as to ready the reservoir for delivering fluid 228 to ejection chamber 224. Upon continued retraction of plunger 212, shoulder 268 contacts transfer passageway seal 264 so as to move the transfer passageway seal from its sealing position.

Figure 4C:
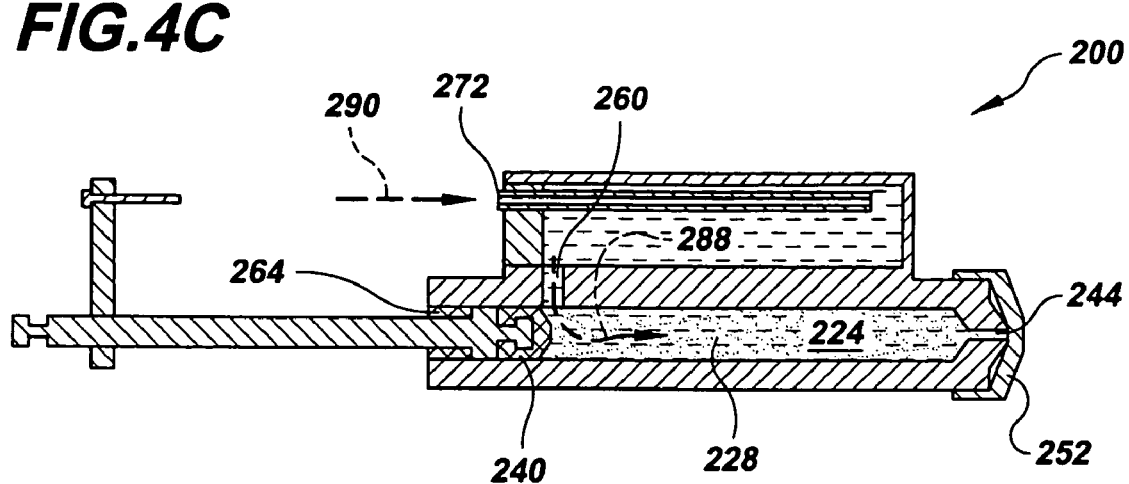
Figure 4D:
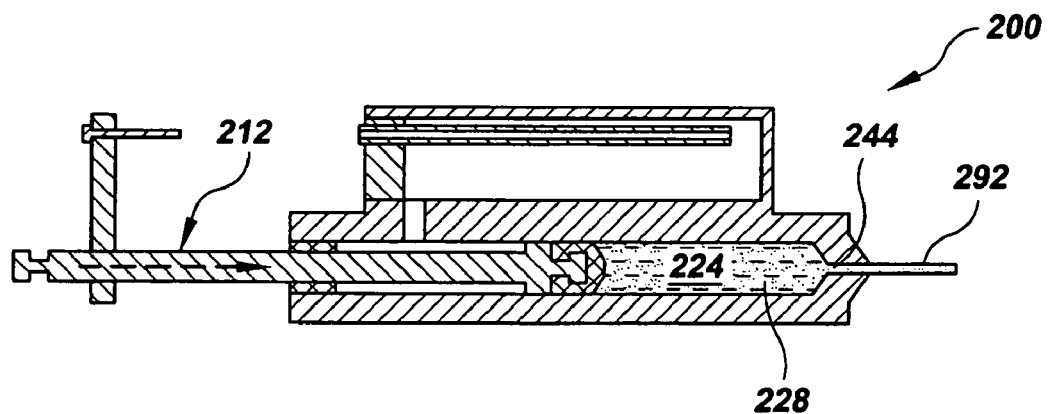

FIG. 4C shows the state of cartridge 200 after transfer passageway seal 264 has been moved and piston 240 has moved past transfer passageway 260. As fluid 228 is sucked into ejection chamber 224 (arrow 288) via transfer passageway 26.0 under influence of the vacuum therein, air enters (arrow 290) via vent 272 to displace fluid 228. Once ejection chamber 224 has been charged, fluid 228 is generally ready to be ejected from cartridge 200. When it is desired to eject fluid 228, cap 252 is removed to unseal outlet 244. Removal of cap 252 may be performed, e.g., either manually or using ejector 32 of FIG. 1. As illustrated in FIG. 4D, plunger 212 may then be pushed into ejection chamber 224, e.g., manually or using ejector 32 of FIG. 1, so as to force fluid 228 out of cartridge 200 through outlet 244 and out therefrom, e.g., in a high pressure stream 292. After fluid 128 has been ejected, cartridge 200 may then be disposed of accordingly or reused.

Figure 5A:
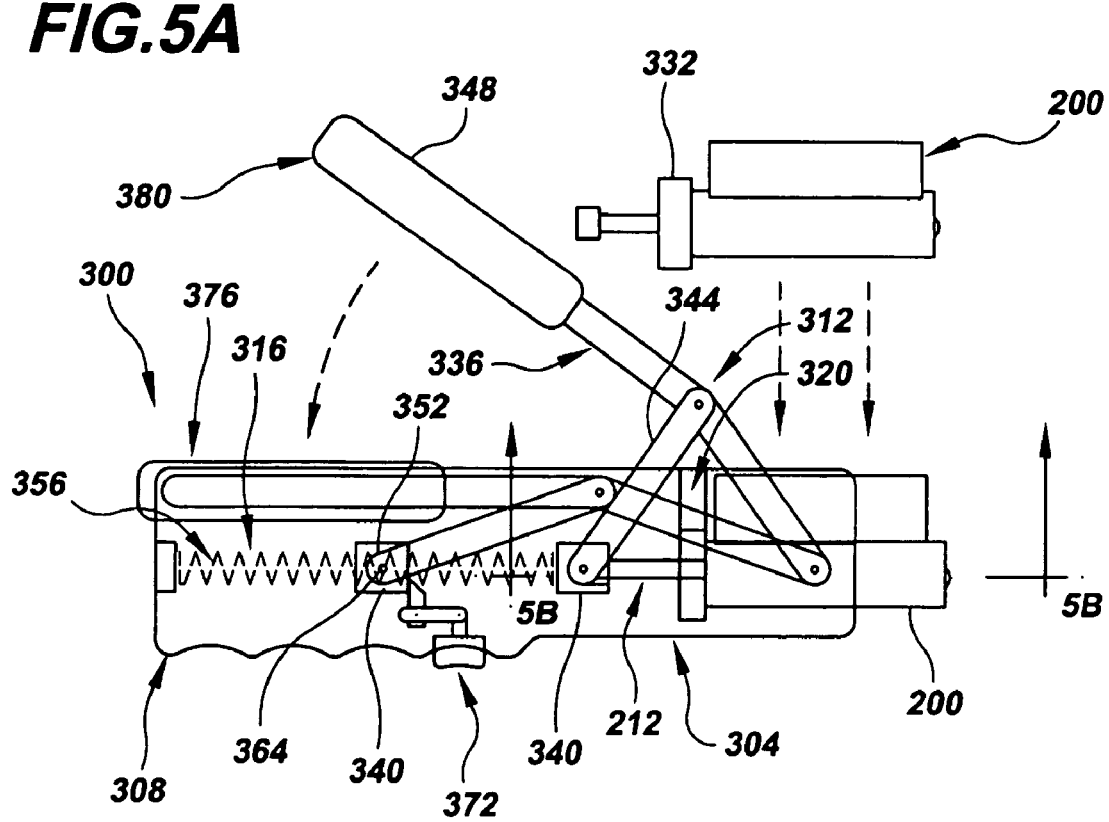
FIG. 5A is a cross-sectional view of a two-way-action ejector that may be used with the fluid ejection system of FIG. 1.

FIG. 5A shows a two-way-action ejector 300 of the present invention that may be used with cartridge 200 of FIGS. 4A-4D as shown, or may be modified to be used with any other of the cartridges disclosed herein. Some of these modifications are described below in the context of cartridges 700 shown in FIGS. 9A-9D et seq., that do not have an integral plunger, but rather have a valve actuator 756 that is retracted prior to ejection of fluid from these cartridges. In addition, ejector 300 may include an integral fluid delivery system (not shown) and a reservoir generally similar to fluid delivery system 124 and reservoir 132 of filling station 24 (FIGS. 1 and 3) for use with cartridge 52 of FIGS. 2A and 2B, or similar cartridges not having on-board reservoirs.

Figure 5B:
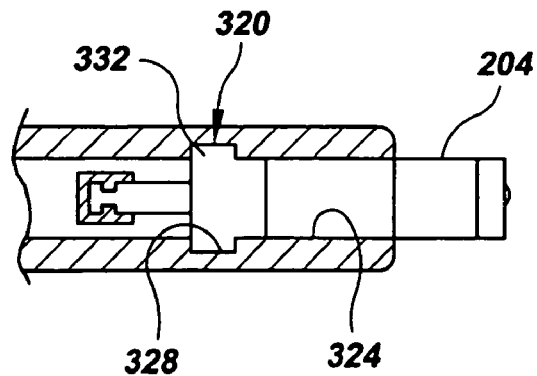
FIG. 5B is an enlarged cross-sectional partial view of the ejector of FIG. 5A as taken along line 5B-5B.

Generally, ejector 300 may comprise a housing 304, a handgrip 308, a retractor mechanism 312 and an ejection mechanism 316. Housing 304 may include a receiver 320 for receiving at least a portion of cartridge 200. As shown in FIG. 5B, receiver 320 may include a longitudinal slot 324, for receiving a portion of housing 204 of cartridge 200, and a transverse slot 328 intersecting the longitudinal slot, for receiving an annular stop 332 on the cartridge so as to inhibit the housing of the cartridge from moving significantly relative to ejector 300 during charging and ejecting of fluid 228. Depending upon the design, housing 304 may substantially or partially contain retractor mechanism 312 and/or ejection mechanism 316. Handgrip 308, or portion thereof, may be formed integrally with housing 304, if desired. Alternatively, handgrip 308 may be formed separately from housing 304 and attached thereto using suitable means.

Referring again to FIG. 5A, retractor mechanism 312 may be a manual system (shown) or an automatic or semi-automatic system, as desired. Various types of manual retractor systems may operate by lever action (shown), ratcheting action, sliding action or screw action, among others. Various types of automatic or semi-automatic systems may operate similarly, but utilize any of a variety of actuators (not shown), including motors, pneumatic actuators and hydraulic actuators, among others. Those skilled in the art will appreciate the wide variety of forms that retractor mechanism 312 may take, such that an exhaustive list is not necessary herein for those skilled in the art to appreciate the broad scope of the present invention. In alternative embodiments for use with, e.g., cartridges 700 of FIGS. 9A-9D et seq., that have a valve actuator, but not a plunger, retractor mechanism 312 may be modified for suitably engaging and retracting the respective valve actuator, rather than engaging and retracting plunger 212.

Still referring to FIG. 5A, and also to FIG. 5B, in the form shown retractor mechanism 312 may include a charging lever 336, a shuttle 340 and a link 344. Charging lever 336 may be pivotably attached to housing 304 and include a handle 348 distal from the housing. Shuttle 340 may include a receiver 352 (FIG. 5C) configured for engaging a portion of plunger 212 so that retractor mechanism 312 can retract the plunger from housing 204 of cartridge 200. Link 344 may be pivotally attached to charging lever 336 at one end and pivotably, but removably, engaged with shuttle 340 at the other end.

Similar to retractor mechanism 312, ejection mechanism 316 may be a manual system, automatic system or a semi-automatic system (shown), and accordingly may include any suitable type of actuator 356 for moving plunger 212 toward end wall 220 of cartridge 200 with the required speed and force necessary to properly eject fluid 228 from cartridge 200. For example, actuator 356 may be of a spring-(shown), lever-, sliding- or screw-type, among others, that may be driven by, e.g., a motor, a pneumatic actuator or a hydraulic actuator, among others. Those skilled in the art will appreciate the wide variety of forms that ejection mechanism 316 may take, such that an exhaustive list is not necessary herein for those skilled in the art to appreciate the broad scope of the present invention.

Continuing to refer to FIG. 5A, and also 5C, in the form shown ejection mechanism 316 may comprise a spring 360, e.g., a coil spring, engaged between housing 304 and shuttle 340. Link 344 of retractor mechanism 312 may be removably engaged with shuttle 340, e.g., by engagement of a pin 364 or similar structure on the link with a slot 368 in the shuttle. Ejection mechanism 316 may also comprise a trigger mechanism 372 for holding shuttle 340 in place once plunger 212 has been sufficiently retracted and/or moving pin 364 out of engagement with slot 368 when the trigger mechanism is actuated.

Ejector 300 may be used as follows to charge cartridge 200 and eject fluid 228 therefrom. First, a user may need to ready ejector 300 for receiving cartridge 200, e.g., by moving charging lever 336 from position 376 to position 380 so that shuttle 340 is in the proper position for receiving plunger 212 in its initial, generally fully-inserted position. Once ejector 300 is ready to receive cartridge 200, the cartridge is engaged with receiver 320 and plunger 212 is engaged with receiver 352 of shuttle 340. These actions may be performed substantially simultaneously with one another as cartridge 200 is engaged with ejector 300. The user may then move handle 348 from position 376 to position 380 so as to retract plunger 212 sufficiently to allow fluid 228 to flow from reservoir 208 to ejection chamber 224 and compress spring 360. Once ejection chamber 224 is sufficiently charged with fluid 228, shuttle 340 will engage trigger mechanism and link 344 can move pin 364 out of engagement with slot 368 of shuttle 340. When user is ready to eject the fluid therefrom, the user may actuate trigger mechanism 372 and release shuttle 340, allowing spring 360 to drive the shuttle and plunger 212 so as to eject fluid 228 from cartridge 200. Once ejection is complete, the user may remove spent cartridge 200, engage another cartridge and repeat the charging and ejecting steps described above.

Figure 6:
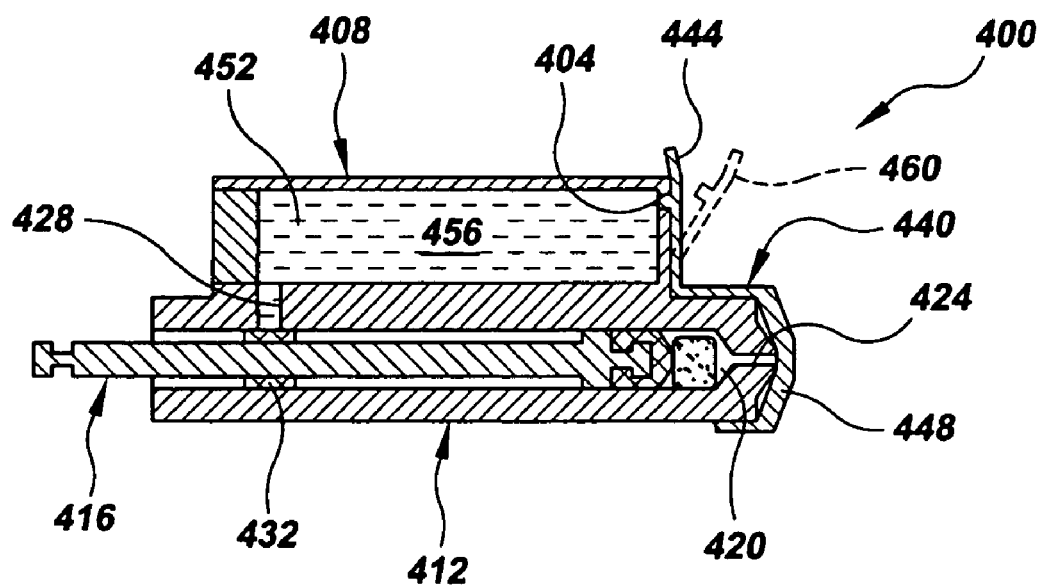
FIG. 6 is cross-sectional view of an alternative offset-reservoir cartridge of the present invention having an integrated vent seal/outlet seal.

FIG. 6 shows a cartridge 400 that is a variation of cartridge 200 of FIGS. 4A-4D, primarily in terms of the location of vent 404 on reservoir 408 and the manner of sealing this vent. Similar to cartridge 200, cartridge 400 of FIG. 6 may include a housing 412, plunger 416, ejection chamber 420, outlet 424, transfer passageway 428 and transfer passageway seal 432, each of which may be the same as or similar to the corresponding parts of cartridge 200 as shown in FIGS. 4A-4D and described in the accompanying description. Unlike vent 272 shown in FIGS. 4A-4D, however, vent 404 of cartridge 400 may be located generally on the "front" of reservoir 408, as shown in FIG. 6. This would readily permit the use of an integrated vent seal/outlet seal, such as integrated seal 440 shown.

Integrated seal 440 may include a vent seal portion 444 and an outlet seal portion 448 that may be actuated separately from one another. In the embodiment shown, integrated seal 440 is relatively flexible so that vent seal portion 440 may be made to unseal vent 404 without outlet seal portion 448 unsealing outlet 424. This is useful because, similar to cartridge 200 discussed above relative to FIGS. 4A-4D, it is desirable to keep outlet 424 sealed until ejection chamber 420 is charged with fluid 452 from reservoir 408, while allowing reservoir chamber 456 to be vented. In alternative embodiments, integrated seal 440 may provide this functionality using another means, such as a hinge.

In general, cartridge 400 may be used in a manner similar to the manner described above in connection with cartridge 200 of FIGS. 4A-4D. The primary difference is with respect to the unsealing of vent 404 and outlet 424 using integrated seal 440. Therefore, this description focuses on this difference. In the initial state of cartridge 400, vent 404 and outlet 424 are sealed, respectively, by vent seal portion 444 and outlet seal portion 448 of integrated seal 440. When it is desired to charge ejection chamber 420 with fluid 452 from reservoir 408, vent seal portion 444 is actuated so as to unseal vent 404 to allow air (or other substance) to enter ejection chamber 420 while the fluid is passing from reservoir chamber 456 to the ejection chamber via transfer passageway 428. Relative to flexible integrated seal 440 shown, vent 404 is unsealed by moving vent seal portion 444 to position 460 shown in FIG. 6. After vent 404 has been unsealed, charging of ejection chamber 420 may proceed substantially as describe in connection with cartridge 200 of FIGS. 4A-4D. When it is desired to eject fluid 452 from ejection chamber 420 once charged, outlet 424 may be unsealed, e.g., by removing integrated seal 440 entirely from cartridge 200. One or both steps of unsealing vent 404 and unsealing outlet 424 may be performed, e.g., either manually or using ejector 32 of FIG. 1.

Figure 7A:
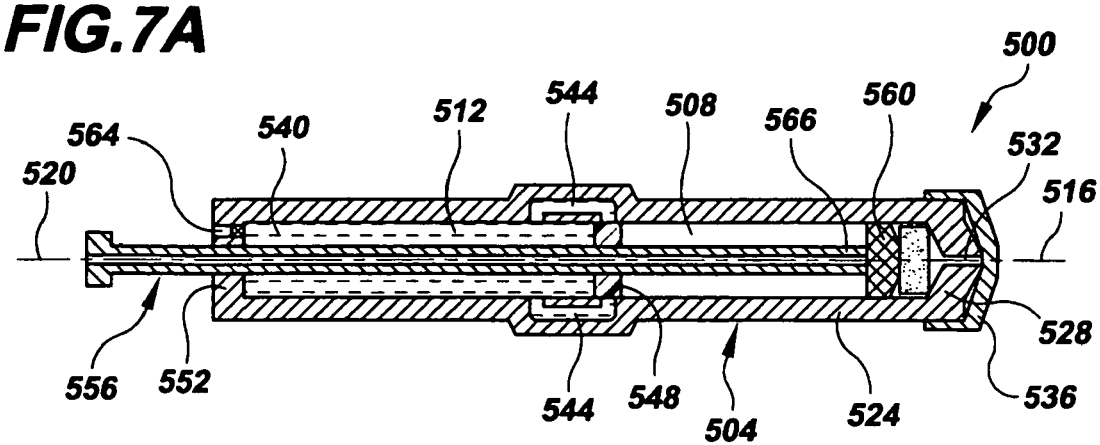
FIGS. 7A-7C are cross-sectional views of a vented inline-reservoir cartridge of the present invention, illustrating its operation.
Figure 7B:
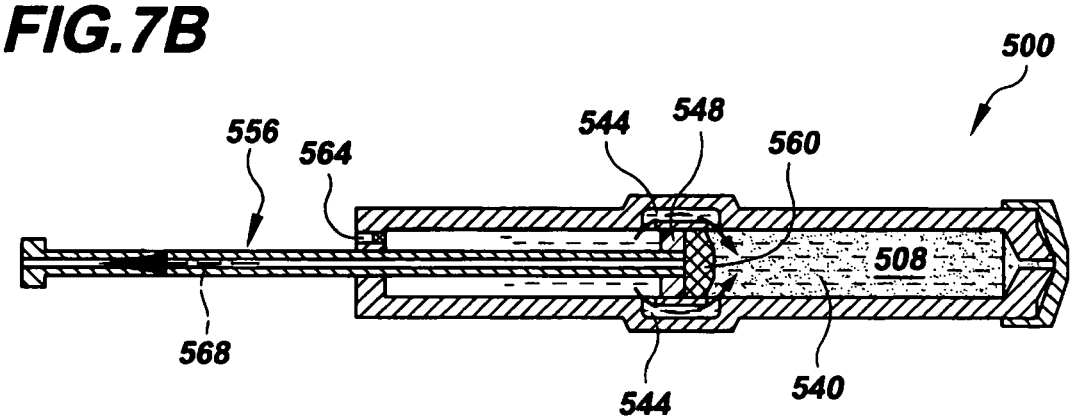
Figure 7C:
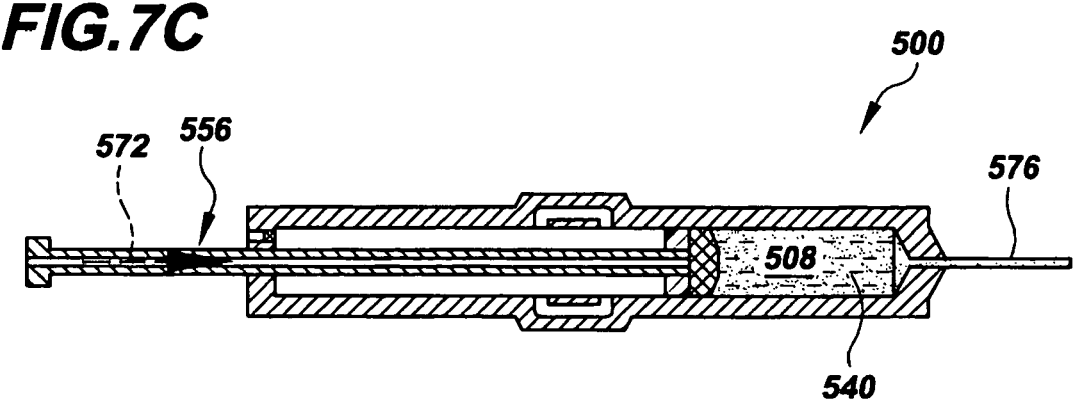

FIGS. 7A-7C show a vented inline-reservoir cartridge 500 of the present invention that may be configured for use with a two-way embodiment of ejector 32 of FIG. 1. Cartridge 500 may include a housing 504 that generally contains an ejection chamber 508 and a reservoir chamber 512 that may be in-line with one another, i.e., wherein the longitudinal central axes 516, 520 of the two chambers are collinear. Housing 504 may comprise a sidewall 524, an end wall 528 and an outlet 532 located, e.g., in the end wall. Housing 504 may be formed as a single part or, alternatively, may be made of any number of parts. Outlet 532 may be sealed with a suitable outlet seal, such as cap 536 shown, plug or frangible seal, among others. If cap 536 is provided, it may be of any suitable type, such as press-fit or threaded, among others. Reservoir chamber 512 is operatively configured for containing a fluid 540 that will eventually be ejected from ejection chamber 508 of cartridge 500. At some point prior to the ejection of fluid from ejection chamber 508, fluid 540 from reservoir chamber 512 must be transferred to the ejection chamber. This may be accomplished by providing one or more transfer passageways 544 that fluidly communicate with each of the two chambers 508, 512. Transfer passageways 544 may be formed in housing 504 or otherwise provided to cartridge 500. To prevent the transfer of fluid at an inappropriate time, transfer passageways 544 may be sealed with one or more transfer passageway seals, such as sealing ring 548 shown, that essentially function as a transfer valve.

Cartridge 500 may also include a plunger seal 552 and a plunger 556 that extends through the plunger seal and sealing ring 548 and includes a piston 560 slidingly engaged within housing 504 in a direction along longitudinal central axes 516, 520. In general, at least initially, reservoir chamber 512 may be said to be defined by sidewall 524 of housing 504, plunger seal 552 and sealing ring 548, whereas ejection chamber 508 may be said to be defined by the sidewall, the sealing ring and end wall 528 of the housing. It is noted that reservoir chamber 512 may need to be vented to allow air (or other substance) to enter the reservoir chamber while fluid 540 is being transferred from the reservoir chamber to ejection chamber 508 and/or to allow air (or other substance) to escape from the reservoir chamber during initiation of the transfer process as discussed below. Thus, a vent 564 may be provided, e.g., in plunger seal 552 or sidewall 524, to provide one or both of these venting functions. A vent 566 also may be provided in plunger 556 to vent chamber 508 during retraction so that seal 548 is not prematurely displaced by pressure buildup.

Cartridge 500 may be used as follows when its initial state is as shown in FIG. 7A, wherein a fluid 540 is located in reservoir chamber 512, piston 560 is located proximate end wall 528 and sealing ring 548 is sealing transfer passageways 544. From this initial state of cartridge 500, as shown in FIG. 7B, plunger 556 may be retracted (arrow 568) within ejection chamber 508 so as to create a vacuum therein. As the retraction of plunger 556 is continued, piston 560, or other portion of the plunger if such portion is provided, contacts sealing ring 548 and moves the ring so as to unseal transfer passageways 544. When plunger 556 is in contact with sealing ring 548, the sealing ring may also provide a seal for vent 566 in the plunger. When fluid 540 in reservoir chamber 512 is incompressible, it may be desirable to provide not only the fluid to the reservoir chamber but also a compressible substance, e.g., a gas, and/or vent 564 to permit sealing ring 548 to be readily moved out of sealing engagement with transfer passageways 544. Once transfer passageways 544 have been unsealed, the vacuum within ejection chamber 508 draws fluid 540 into this chamber. Referring to FIG. 7C, after ejection chamber 508 has been charged with fluid 540 and it is desired to eject the fluid from cartridge 500, cap 536 (FIG. 7A) is removed and plunger 556 is depressed (arrow 572) so as to eject the fluid from the ejection chamber via outlet 532, e.g., as a fluid stream 576.

Figure 5C:
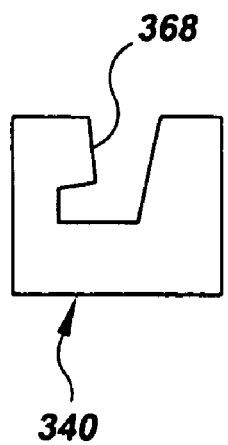
FIG. 5C is an enlarged elevational view of the shuttle of the ejector of FIG. 5A.
Figure 8E:
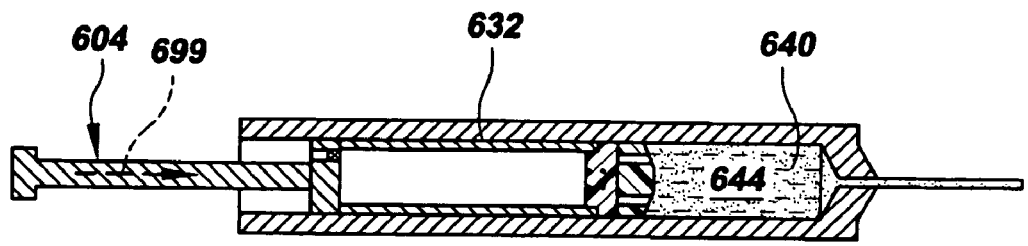

FIGS. 8A-8E show an alternative vented inline-reservoir cartridge 600 of the present invention that may be configured for use with a two-way-action embodiment of ejector 32 of FIG. 1, e.g., ejector 300 of FIGS. 5A-5C. Referring particularly to FIG. 8A, cartridge 600 may include a plunger 604 and a housing 608 that generally defines an elongate cavity 612. Housing 608 may include a sidewall 616, an end wall 620 and an outlet 624 located, e.g., in the end wall. Plunger 604 may include a piston 628 and a reservoir 632 defining a reservoir chamber 636 for containing a fluid 640 to be transferred to an ejection chamber 644 formed within cavity 612 prior to the fluid being ejected from cartridge 600. Reservoir 632 may include a sidewall 648 and first and second end walls 652, 656 joined to the sidewall and spaced from one another. Reservoir chamber 636 may extend along substantially the entire length of plunger 604, or may extend a smaller portion of the length of the plunger as shown. In the latter case, plunger 604 may also include an extension 660 that makes the plunger a suitable length. Piston 628 is slidingly engaged with housing 608 within cavity 612. When piston 628 is spaced from end wall 620, e.g., as shown in FIG. 8B, sidewall 616 and the end wall of housing 608 and the piston define ejection chamber 644. Reservoir chamber 636 may be in-line with ejection chamber 644, i.e., the longitudinal central axes 664, 668 of the two chambers may be collinear.

Outlet 624 may be any suitable type of outlet, such as a high-pressure nozzle, a low-pressure nozzle or a passageway in fluid communication with another member, such as a hypodermic needle or tube, among others. Outlet 624 may be sealed with a suitable outlet seal, such as cap 672 shown, plug or frangible seal, among others. If cap 672 is provided, it may be of any suitable type, such as press-fit or threaded, among others.

At some point prior to the ejection of fluid from ejection chamber 644, fluid 640 from reservoir chamber 636 will be transferred to the ejection chamber. However, until that time, it is desirable to keep fluid 640 sealed within reservoir chamber 636. In order to achieve these functions, plunger 604 may be provided with a transfer valve 676 that is initially closed, but can be opened when charging of ejection chamber 644 is desired. In one embodiment, transfer valve 676 may be formed using second end wall 656 of reservoir 632 and piston 628 by providing these parts with corresponding apertures 680, 684 that may be selectively placed in and out of registration with one another. This may be accomplished, e.g., by making reservoir 636 and extension 660 rotatable about longitudinal central axis 668 relative to piston 628, which tends to resist rotation due to its generally snug engagement with housing 608. As those skilled in the art will appreciate, reservoir 632 and extension 660 may be made rotatable relative to piston 628 using any of a number of rotatable mechanical connections (not shown). When apertures 680, 684 are in registration with one another, transfer valve 676 is open, and fluid 640 may flow from reservoir chamber 636 to ejection chamber 644. Conversely, when apertures 680, 684 are completely out of registration with one another, transfer valve 676 is closed, and fluid 640 may not flow. It is noted that reservoir chamber 636 may need to be vented to allow air (or other substance) to enter the reservoir chamber while fluid 640 is being transferred from the reservoir chamber to ejection chamber 644. Thus, a vent 688 may be provided, e.g., in first end wall 656 or sidewall 648 of reservoir 632 depending upon the design, to provide this venting.

Cartridge 600 may be used as follows when its initial state is as shown in FIG. 8A, wherein piston 628 is located proximate end wall 620, cap 672 is sealing outlet 624, reservoir chamber 636 contains fluid 640 and transfer valve 676 is closed, i.e., apertures 680, 684 are completely out of registration with one another. Referring to FIG. 8B, plunger 604 may be retracted (arrow 692), creating a vacuum in ejection chamber 644. Once plunger 604 has been retracted an appropriate amount, e.g., based on the amount of fluid 640 to be ejected, transfer valve 676 may be opened, e.g., as shown in FIG. 8C, by rotating reservoir 632 and extension 660 relative to piston 628 (arrow 6994) so that apertures 680, 684 move into registration with one another. The vacuum within ejection chamber 644 will then draw fluid 640 into the ejection chamber from reservoir chamber 636 via apertures 680, 684 (arrows 696), while air (arrow 697) enters the reservoir chamber to displace the fluid that charges the ejection chamber.

As shown in FIG. 8D, once ejection chamber 644 has been suitably charged with fluid 640, transfer valve 676 may be closed by rotating reservoir 632 and extension 660 (arrow 698) relative to piston 628 so as to take apertures 680, 684 out of registration with one another. In order to eject fluid 640 from ejection chamber 644, cap 672 (FIG. 8A) is removed, and plunger 604 is depressed (arrow 699 as shown in FIG. 8E) to force fluid 640 out of the ejection chamber. It is noted that if more fluid 640 remains in reservoir 632 after a portion of the fluid has been ejected, cap 672 may be replaced and the above procedure repeated to eject more fluid from ejection chamber 644. This can continue until reservoir 632 is empty or the amount of fluid 640 remaining for the last iteration is insufficient for the intended application.

Figure 9A:
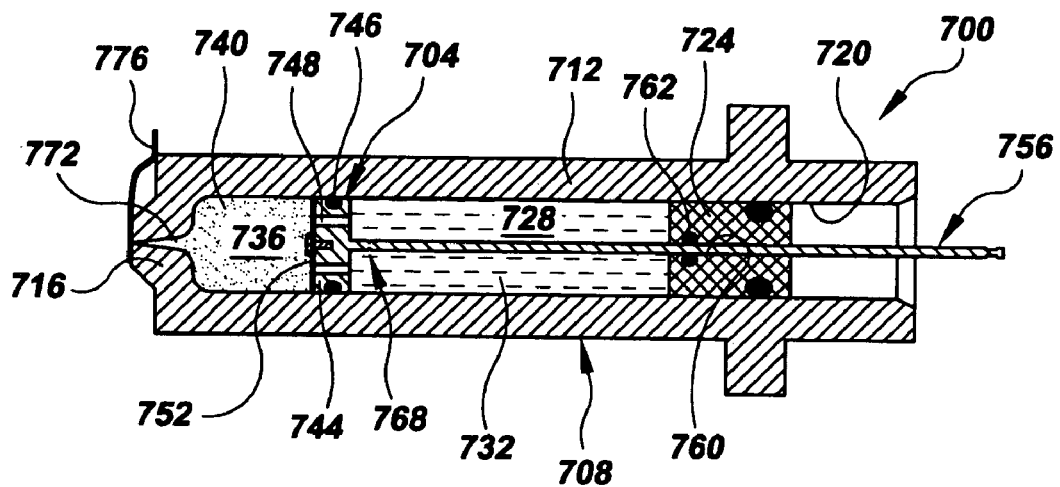
FIGS. 9A-9D are cross-sectional views of a traveling-valve inline-reservoir cartridge of the present invention, illustrating its operation.

FIGS. 9A-9D illustrate a cartridge 700 of the present invention that includes a traveling valve 704. Cartridge 700, like all other cartridges disclosed herein, may be used with an ejector 32 of FIG. 1, e.g., when such ejector is either a one-way-action or a two-way-action ejector configured appropriately. Use of cartridge 700 with these embodiments of ejector 32 of FIG. 1 are described below. Referring first to FIG. 9A, cartridge 700 may comprise a housing 708 that includes a sidewall 712 and an end wall 716 that generally define a cavity 720 within the housing. A piston 724 may be slidingly sealingly engaged with housing 708 within cavity 720 and, at least initially, may be located distal from end wall 716 so as to generally define at least a first chamber 728 within cartridge 700. In the embodiment shown, first chamber 728 functions as a reservoir chamber that contains a fluid 732 to be ejected from cartridge 700. As those skilled in the art will appreciate, piston 724 may be a unitary member configured to sealingly engage sidewall 712 of housing 708, or the proper seal may be effected using one or more additional members, such as an O-ring (not shown).

Traveling valve 704 is located between end wall 716 and piston 724, e.g., in spaced relation to the end wall and piston so as to define not only first chamber 728, but a second chamber 736 as well. Second chamber 736 need not be present initially. In this case, traveling valve 704 would be in contact, or nearly so, with end wall 716. However, when second chamber 736 is present, it may contain, at least initially, a material 740 to be mixed with fluid 732 from first chamber 728 prior to ejection in the manner described below. Fluid 732 and material 740 may be as described above in connection with cartridge of FIGS. 4A-4D.

Traveling valve 704 may include generally a valve piston 744 movable relative to housing 708. Depending upon the design of valve piston 744, the piston itself may slidingly/sealingly engage sidewall 712 of housing 708, or a seal may be effected between the piston and sidewall using a suitable sliding/sealing member, such as O-ring 746. Those skilled in the art will appreciate the variety of ways in which an effective seal may be made by or between valve piston 744 and sidewall 712 such that there is no need to list all alternatives herein for those skilled in the art to appreciate the broad scope of the present invention. Valve piston 744 may include a plurality of apertures 748 for passing fluid 732 from first chamber 728 to second chamber 736 when traveling valve 704 is actuated as described below. Traveling valve 704 may further include one or more temporary seals for sealing aperture(s) 748 until the valve is actuated. For example, as shown, temporary seal may be a flexible disc 752 located on the side of valve piston 744 proximate end wall 716. Flexible disc 752 may seal apertures 748 in any suitable manner, e.g., as a result of being pressed against material 740 (or end wall 716 if this material is not present), by virtue of its own stiffness and/or being adhered to valve piston 744, e.g., using a relatively weak adhesive, among others. The temporary seal, however, may be other than flexible disc 752, such as a rigid "flapper" valve or frangible seal, among others.

Traveling valve 704 may be actuated by a valve actuator 756. The valve actuator 756 may be attached to traveling valve 704 in any suitable manner and extend sealingly through piston 724, e.g., through an aperture 760 and, optionally, an O-ring 762 or similar seal in the aperture. Valve actuator 756 may be a rigid rod or elongate flexible member, e.g., a string, cord, cable or filament, among others. If desired, valve actuator 756 may be made frangible at a desired location and under certain conditions so as to not interfere with the ejection of fluid 732. For example, valve actuator 756 may be made to include a stress concentrator 768, e.g., a neck, notch or depression, among others, that will cause the valve actuator to break at the location of the stress concentrator under the appropriate conditions. This is described below in more detail in conjunction with the operation of cartridge 700.

Cartridge 700 may further include an outlet 772 for passing liquid 732 or the liquid mixed with material 740, if provided, out of the cartridge during ejection. Outlet 772 may be located, e.g., in end wall 716, and may be of any suitable type, such as a high-pressure nozzle, a low-pressure nozzle or a passageway in fluid communication with another member, such as a hypodermic needle or tube, among others. Outlet 772 may be sealed with a suitable outlet seal, such as peel-away seal 776 shown, cap, plug or frangible seal, among others.

Figure 9B:
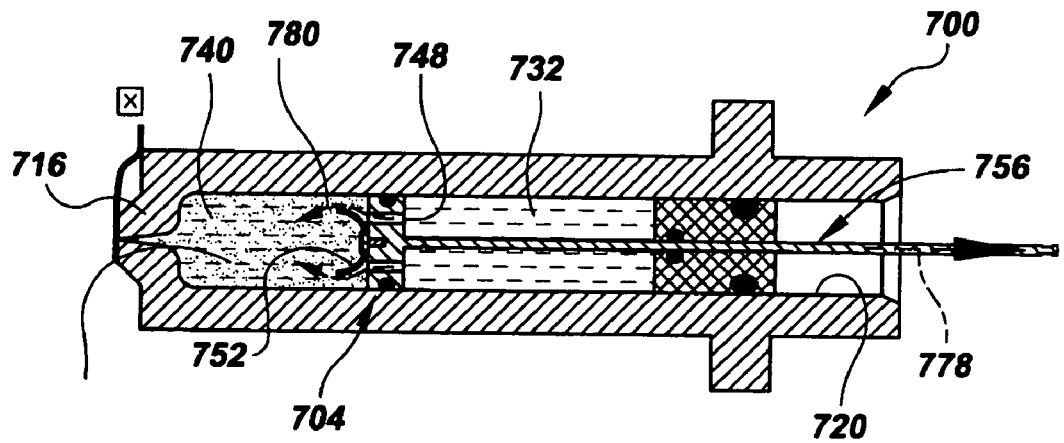

Cartridge 700 may be used as follows. With continuing reference to FIG. 9A, this figure illustrates an initial state of cartridge 700, wherein fluid 732 is contained in first chamber 728, material is contained in second chamber 736, traveling valve 704 is located immediately adjacent to the material, flexible disc 752 is sealing apertures 748 in valve piston 744 and peel-away seal 776 is sealing outlet 772. To initiate mixing of fluid 732 with material 740, as shown in FIG. 9B, valve actuator 756 is retracted within cavity 720 so as to move traveling valve 704 in a direction away from end wall 716, as indicated by arrow 778. Valve actuator 756 may be retracted manually, with a dedicated retractor (not shown) or an ejector, such as ejector 32 of FIG. 1. In the case of retraction by ejector 32, the ejector would generally be a two-way-action ejector having a mechanism operatively configured for engaging valve actuator 756 and retracting the actuator. As valve actuator 756 continues to be retracted, the pressure of fluid 732 within first chamber 728 caused by the movement of traveling valve 704 acts against flexible disc 752, and any adhesive that may be present, thereby opening the valve. As seen in FIG. 9B, the opening of traveling valve 704 allows fluid 732 to pass through apertures 748 in valve piston 744 into second chamber 736 (as indicated by arrows 780), wherein such fluid mixes with material 740.

Figure 9C:
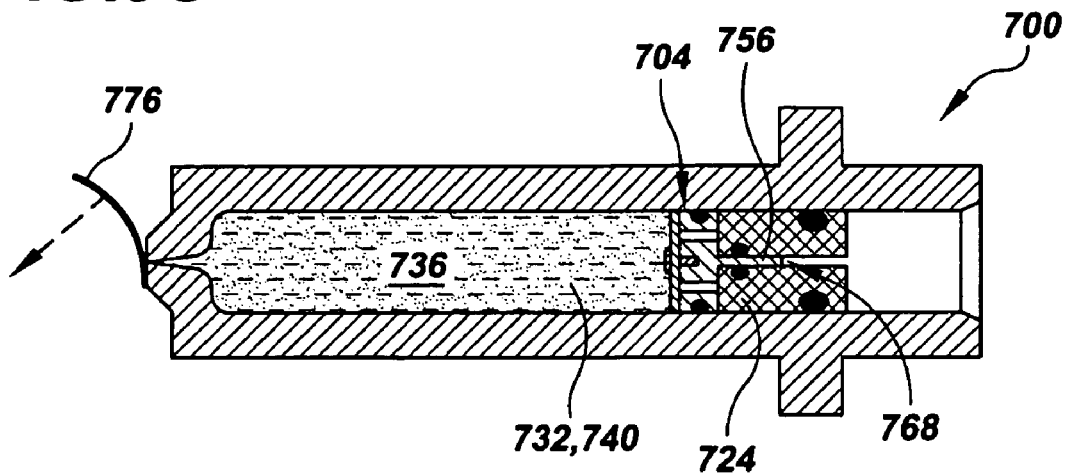

Retraction of valve actuator 756 may be continued until traveling valve 704 contacts piston 724 as shown in FIG. 9C.
At this point, substantially all of fluid 732 that was initially contained in first chamber 728 has essentially been transferred to second chamber 736, which has become greater in size due to the displacement of traveling valve 704. Depending upon the manner in which fluid 732 and material 740 will be ejected from cartridge 700, valve actuator 756, or portion thereof, may be removed so as to not interfere with the ejection process. As mentioned above, valve actuator 756 may be provided with stress concentrator 768 that sufficiently stresses the actuator upon contact with piston 724 that the actuator breaks at the stress concentrator. The broken-off portion of valve actuator 756 may then be removed and discarded, as shown in FIG. 9C. In alternative embodiments, valve actuator 756 may be severed using a severing device (not shown) that is either integral with or separate from cartridge 700, or may otherwise be removable.

Figure 9D:
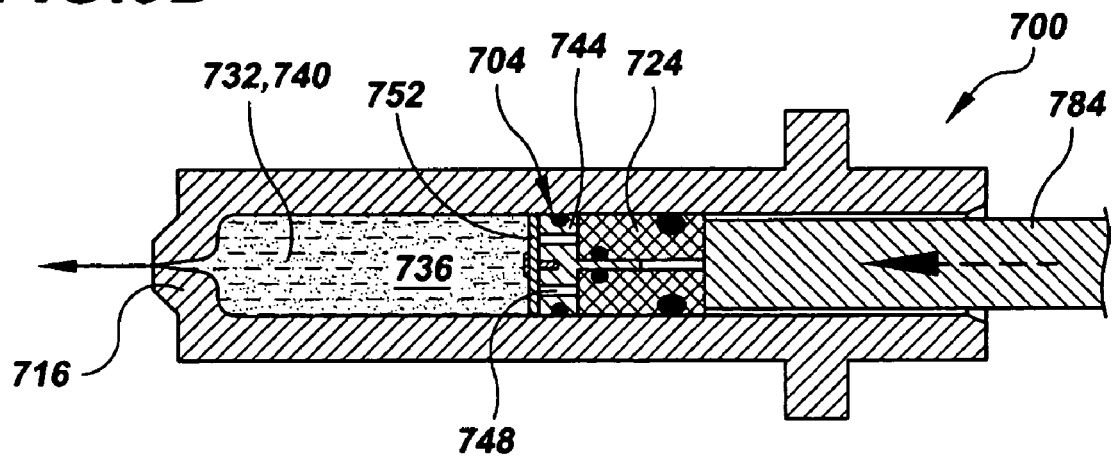

Just prior to ejection, peel-away seal 776 may be removed to allow ejection of fluid 732 and material 740 from cartridge 700. As shown in FIG. 9D, ejection may be effected by pushing piston 724 toward end wall 716, e.g., using a plunger 784. As traveling valve 704 is pushed toward end wall 716, flexible disc 752 seals apertures 748 in valve piston 744 as a result of the induced pressure against fluid 732 and material 740 in second chamber 736. If valve seal(s) were frangible, passageways would remain open upon ejection. However, in this case, piston 724 would provide the necessary seal for pressurizing fluid 732 and material 740 in second chamber 736. Plunger 784 may be separate from piston 724 as shown or integral with the piston in a manner similar to piston 76 and plunger 60 described above relative to cartridge 52 of FIG. 2A, among others. If plunger 784 is separate from piston 724, it may be part of an ejector, e.g., ejector 32 of FIG. 1. If plunger 784 is integral with piston 724, valve actuator 756 (see FIGS. 9A and 9B) may extend at least partway through the plunger to allow for moving traveling valve 704.

Figure 10A:
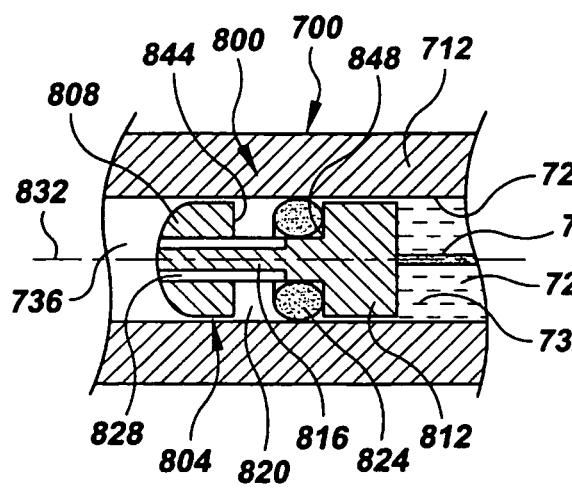
FIGS. 10A and 10B are enlarged cross-sectional partial views of an alternative traveling valve that may be used in place of the traveling valve shown in FIGS. 9A-9D.
Figure 10B:
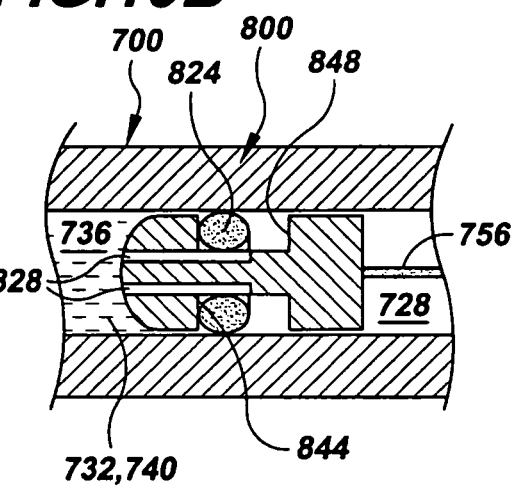

FIGS. 10A and 10B illustrate an alternative traveling valve 800 that may be used in cartridge 700 of FIGS. 9A-9D in lieu of traveling valve 704. Traveling valve 800 may be viewed as a sliding O-ring valve that includes a member 804 having a head 808, body 812 and neck 816 that defines an annular channel 820 that contains an O-ring 824, or ring of another shape depending upon the transverse cross-sectional shape of cavity 720 (FIG. 9A). Head 808 and a portion of neck 816 adjacent the head include one or more passageways 828 for allowing fluid 732 from first chamber 728 to pass to second chamber 736 when traveling valve 800 is open. In this connection, O-ring 824 is generally compressed between neck 816 and sidewall 712 and is movable in a direction along the longitudinal central axis 832 within annular channel 820 between a sealed position (FIG. 10A) and an unsealed position (FIG. 10B).

Traveling valve 800 may be actuated as follows. When valve 800 is initially sealed as shown in FIG. 10A, valve actuator 756 is retracted, thereby causing member 804 to move toward the right in FIG. 10A. When member 804 is initially moved to the right, O-ring 824 tends to not move until contacted by sidewall 844 of annular channel 820, at which time the O-ring is in its unseal position 840 of FIG. 10B, wherein passageways 828 are in fluid communication with both first and second chambers 728, 736. As valve actuator 756 is continued to be retracted, O-ring 824 remains in contact with sidewall 848 of annular channel 820, keeping traveling valve 800 open.

Once traveling valve 800 reaches the end of its travel upon the retraction of valve actuator 756, O-ring 824 will typically be in its unsealed position 840 shown in FIG. 10B. To eject fluid 732 and material 740 from cartridge 700, traveling valve 800 is moved in the opposite direction, i.e., to the left in FIGS. 10A and 10B, which initially causes member 804 to move while O-ring 824 tend to remain stationary. However, once member 804 is moved sufficiently, O-ring 824 contacts sidewall 848 of annular channel 820, closing traveling valve 800. Even if O-ring 824 did not return to its sealed position, piston 724 (FIG. 9A) would provide the necessary seal for pressurizing fluid 732 in second chamber 736. It is noted that neck 816 of traveling valve 800 may be designed so as to fail, i.e., break, in compression at the end of the ejection stroke of the valve as head 808 impacts end wall 716 (FIG. 9A) of housing 708. This is a safety feature that would prevent cartridge 700 from being reused.

Figure 11A:
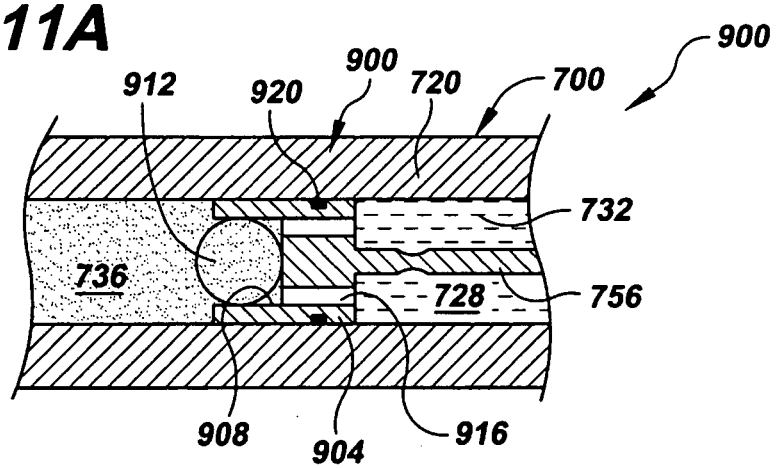
FIGS. 11A and 11B are enlarged cross-sectional partial view of another alternative traveling valve that may be used in place of the traveling valve shown in FIGS. 9A-9D.
Figure 11B:
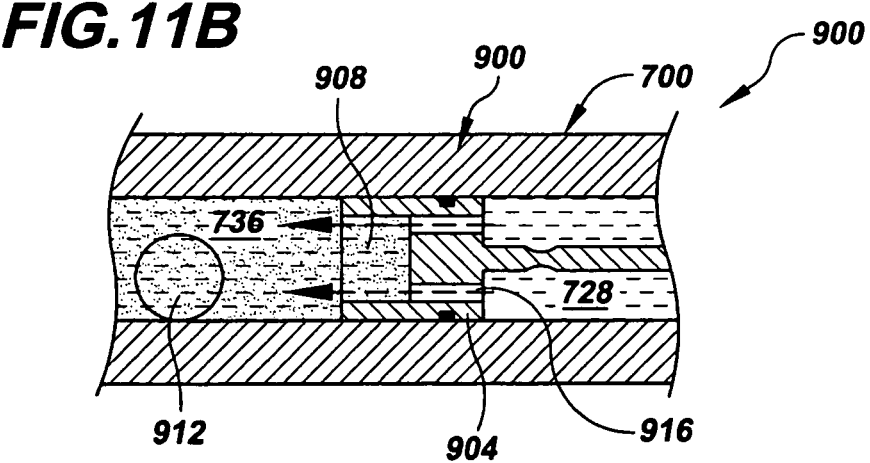

FIGS. 11A and 11B illustrate another alternative traveling valve 900 that may be used in cartridge 700 of FIGS. 9A-9D in lieu of traveling valve 704. Traveling valve 900 may include a valve piston 904 that defines a socket 908 for sealingly receiving a removable stopper 912, such as a ball or other body. Valve piston 904 may include one or more passageways 916 each in fluid communication with both socket 908 and first chamber 728 for passing fluid 732 from the first chamber to second chamber 736 when valve 900 is open, i.e., when stopper 912 is disengaged from the socket. Valve piston 904 itself may slidingly/sealingly engage sidewall 712 of housing 708, or a seal may be effected between the piston and sidewall using a suitable sliding/sealing member, such as an O-ring 920. Those skilled in the art will appreciate the variety of ways in which an effective seal may be made by or between piston and sidewall such that there is no need to list all alternatives herein for those skilled in the art to appreciate the broad scope of the present invention.

Traveling valve 900 may be actuated as follows. When valve 900 is initially sealed as shown in FIG. 11A, valve actuator 756 is retracted, thereby causing valve piston 904 to move toward the right in FIG. 11A. As valve piston 904 is moved, pressure within first chamber 728 is increased, finally to a point where stopper 912 disengages socket 908 as fluid 732 is forced through passageways 916. Once disengaged from socket, stopper 912 may be free to move about second chamber 936 as shown in FIG. 11B. Consequently, stopper 912 can be utilized as a mixing aid, if desired, by moving cartridge 700 in a manner that moves the stopper about second chamber 736.

Figure 12A:
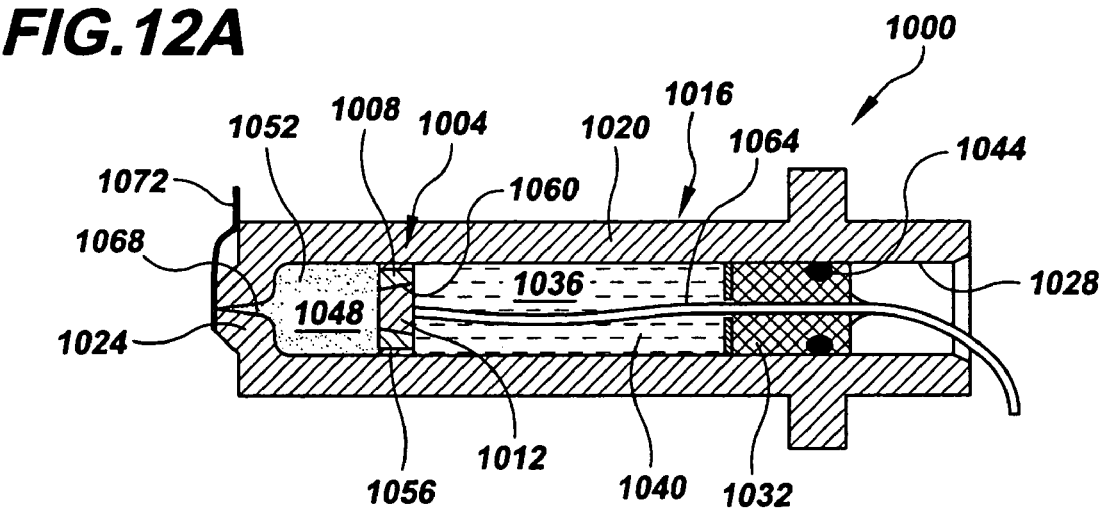
FIGS. 12A-12D are cross-sectional views of an inline-reservoir cartridge of the present invention having a temporarily stationary valve, illustrating its operation.

FIGS. 12A-12D shows a non-vented inline-reservoir cartridge 1000 having an internal valve 1004 that includes a temporarily stationary valve member 1008 and a removable valve member 1012 initially engaged with, or attached to, the stationary valve member. Referring first to FIG. 12A, like other cartridges discussed above, cartridge 1000 may comprise a housing 1016 that includes a sidewall 1020 and an end wall 1024 that generally define a cavity 1028 within the housing. A piston 1032 may be slidingly sealingly engaged with housing 1016 within cavity 1028 and, at least initially, may be located distal from the end wall 1024 so as to generally define at least a first chamber 1036 within cartridge 1000. In the embodiment shown, first chamber 1036 functions as a reservoir chamber that contains a fluid 1040 to be ejected from cartridge 1000. As those skilled in the art will appreciate, piston 1032 may be a unitary member configured to sealingly engage sidewall of housing, or the proper seal may be effected using one or more additional members, such as O-ring 1044.

Valve 1004 may be located between end wall 1024 and piston 1032, e.g., in spaced relation to the end wall and piston so as to define not only first chamber 1036, but also a second chamber 1048. Second chamber 1048 need not be present initially. In this case, valve 1004 would be in contact, or nearly so, with end wall 1024. However, when second chamber 1048 is present, it may contain, at least initially, a material 1052 to be mixed with fluid 1040 from first chamber 1036 prior to ejection in the manner described below. Fluid 1040 and material 1052 may be as described above in connection with cartridge 200 of FIGS. 4A-4D.

Stationary valve member 1008 may be held in place by a friction/sealing fit with sidewall 1020 of housing 1016, with or without an O-ring (not shown) or a sealant 1056 applied to the joint between these parts. If sealant 1056 is used, the bond formed thereby is preferably of a strength that allows piston 1032 to break the bond during the ejection phase, as discussed below in more detail. Stationary valve member 1008 may include at least one opening 1060 for passing fluid 1040 from first chamber 1036 to second chamber 1048 when removable valve member 1012 is removed. Removable valve member 1012 may be any type of member for sealing opening(s), such as the plug-type member shown. When removable valve member 1012 is a plug, it and/or stationary valve member 1008 may be made out of a relatively compressible material that creates a fluid seal when the removable valve member is engaged with opening 1060. Alternatively, stationary valve member 1008 and/or removable valve member 1012 may be provided with one or more O-rings (or other suitably-shaped seals) for ensuring a fluid seal. In alternative embodiments, removable valve member 1012 may be of another type, such as a member that is frangibly or adhesively attached to stationary valve member 1008, among others. Valve 1004 may be actuated by a valve actuator 1064 attached to removable valve member 1012. Valve actuator 1064 may be the same as or similar to actuator 756 described above in connection with FIGS. 9A-9D.

Cartridge 1000 may further include an outlet 1068 for passing liquid 1040 or liquid mixed with material 1052, if provided, out of the cartridge during ejection. Outlet 1068 may be located, e.g., in end wall, and may be of any suitable type, such as a high-pressure nozzle, a low-pressure nozzle or a passageway in fluid communication with another member, such as a hypodermic needles or tube, among others. Outlet may be sealed with a suitable outlet seal, such as peel-away seal 1072 shown, cap, plug or frangible seal, among others.

Figure 12B:
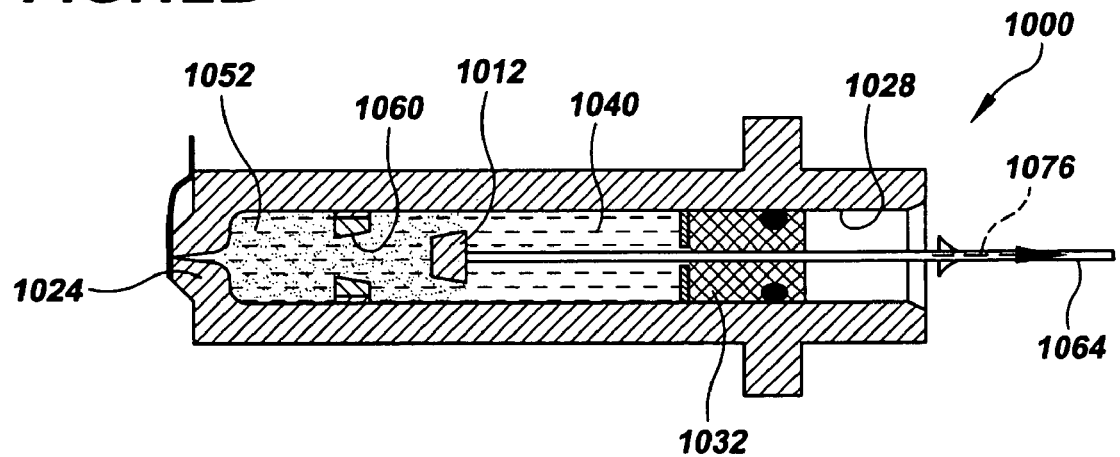

Cartridge 1000 may be used as follows. With continuing reference to FIG. 12A, this figure illustrates an initial state of cartridge 1000, wherein fluid 1040 is contained in first chamber 1036, material 1052 is contained in second chamber 1048, valve 1004 is located immediately adjacent the material, removable valve member 1012 is sealing opening 1060 in stationary valve member 1008 and peel-away seal 1072 is sealing outlet 1068. To initiate mixing of fluid 1040 with material 1052, as shown in FIG. 12B, valve actuator 1064 is retracted within cavity 1028 so as to move removable valve member 1012 in a direction away from end wall 1024, (arrow 1076). Valve actuator 1064 may be retracted manually, with a dedicated retractor (not shown) or an ejector, such as ejector 32 of FIG. 1. In the case of retraction by ejector 32, the ejector would generally be a two-way-action ejector having a mechanism operatively configured for engaging valve actuator and retracting the actuator. Once opening 1060 is unsealed, fluid 1040 and material 1052 are free to mix with one another.

Figure 12C:
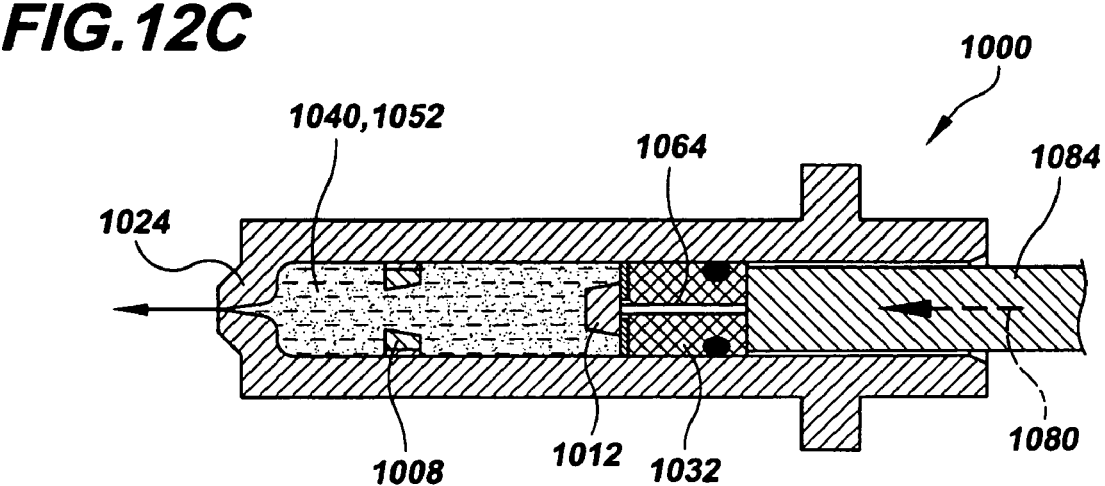

Retraction of valve actuator 1064 may be continued until removable valve member 1012 contacts piston 1032. Depending upon the manner in which fluid 1040 and material 1052 will be ejected from cartridge 1000, valve actuator 1064, or portion thereof, may be removed so as to not interfere with the ejection process. As mentioned above, valve actuator 1064 may be provided with a stress concentrator (not shown) that sufficiently stresses the actuator upon contact with piston 1032 such that the actuator breaks at the stress concentrator. The broken-off portion of valve actuator 1064 may then be removed, as shown in FIG. 12C. In alternative embodiments, valve actuator 1064 may be severed using a severing device that is either integral with or separate from cartridge 1000, or may otherwise be removable.

Figure 12D:
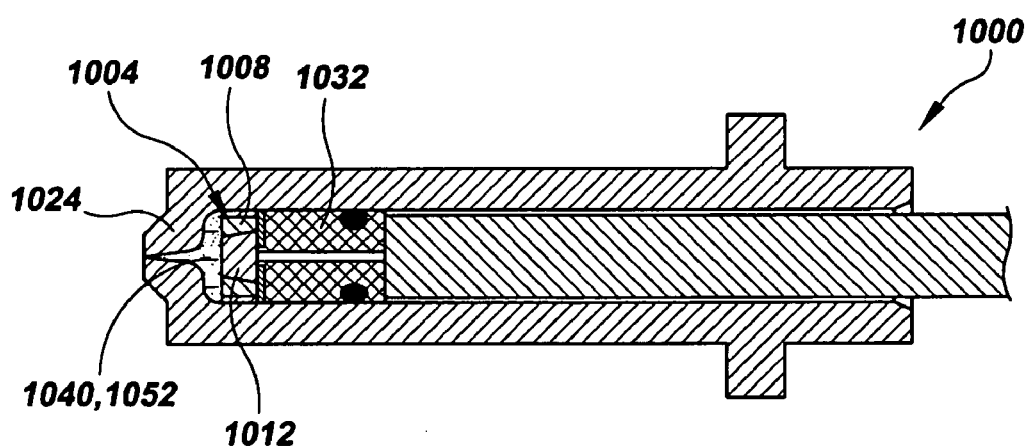

Just prior to ejection, peel-away seal 1072 may be removed to allow ejection of fluid 1040 and material 1052 from cartridge 1000. As shown in FIG. 12C, ejection may be effected by pushing piston 1032 toward end wall 1024 (arrow 1080), e.g., using a plunger 1084. Plunger 1084 may be separate from piston 1032 as shown or integral with the piston in a manner similar to piston and plunger described above relative to cartridge 52 of FIG. 2A, among others. If plunger 1084 is separate from piston 1032, it may be part of an ejector, e.g., ejector 32 of FIG. 1. If plunger 1084 is integral with piston 1032, valve actuator 1064 (see FIGS. 12A and 12B) may extend at least partway through the plunger to allow for removable valve member. As piston 1032 is continued to be pushed toward end wall 1024, it contacts and then pushes stationary valve member 1008 toward the end wall until ejection of fluid 1040 and/or material 1052 is complete or the desired amount of the fluid and/or material has been ejected. FIG. 12D shows traveling valve 1004 at the end of its travel adjacent end wall 1024, with removable valve member 1012 engaged with stationary valve member 1008.

FIGS. 13A-13D shows a non-vented inline-reservoir cartridge 1100 having an internal valve 1104 that includes a expandable plug 1108 and a movable wedge 1112. Referring first to FIG. 12A, like other cartridges discussed above, cartridge 1000 may comprise a housing 1116 that includes a sidewall 1120 and an end wall 1124 that generally define a cavity 1128 within the housing. A piston 1132 may be slidingly sealingly engaged with housing 1116 within cavity 1128 and, at least initially, may be located distal from end wall 1124 so as to generally define at least a first chamber 1136 within cartridge 1000. In the embodiment shown, first chamber 1136 functions as a reservoir chamber that contains a fluid 1140 to be ejected from cartridge 1000. As those skilled in the art will appreciate, piston 1132 may be a unitary member configured to sealingly engage sidewall of housing 1116, or the proper seal may be effected using one or more additional members, such as O-ring 1044.

Valve 1104 is shown located between end wall 1124 and piston 1132, e.g., in spaced relation to the end wall and piston so as to define not only first chamber 1136, but also a second chamber 1148. However, second chamber 1148 need not be present initially. In this case, valve 1104 would be in contact, or nearly so, with end wall 1124. However, when second chamber 1148 is present, it may contain, at least initially, a material 1152 to be mixed with fluid 1140 from first chamber 1136 prior to ejection in the manner described below. Fluid 1140 and material 1152 may be as described above in connection with FIG. 1.

Expandable plug 1108 may be made of a stretchable material, such as an elastomer, and include one or more cavities 1156 containing at least a portion of movable wedge 1112. When valve 1104 is closed, movable wedge 1112 is pressed into cavity 1156 so as to cause expandable plug 1108 to expand so as to force the expandable plug into sealing contact with sidewall 1120 of housing 1116. In this connection, movable plug 1112 and cavity 1156 may have complementary tapered surfaces 1160, 1164. When valve 1104 is open, movable plug 1112 is withdrawn at least partially from cavity 1156 so as to allow expandable plug 1108 to retract, thereby reducing the outside diameter of the expandable plug to a value less than the inside diameter of cavity 1128 so as to form a passageway 1168 (FIGS. 13B and 13C) between first and second chambers 1136, 1148.

Figure 13A:
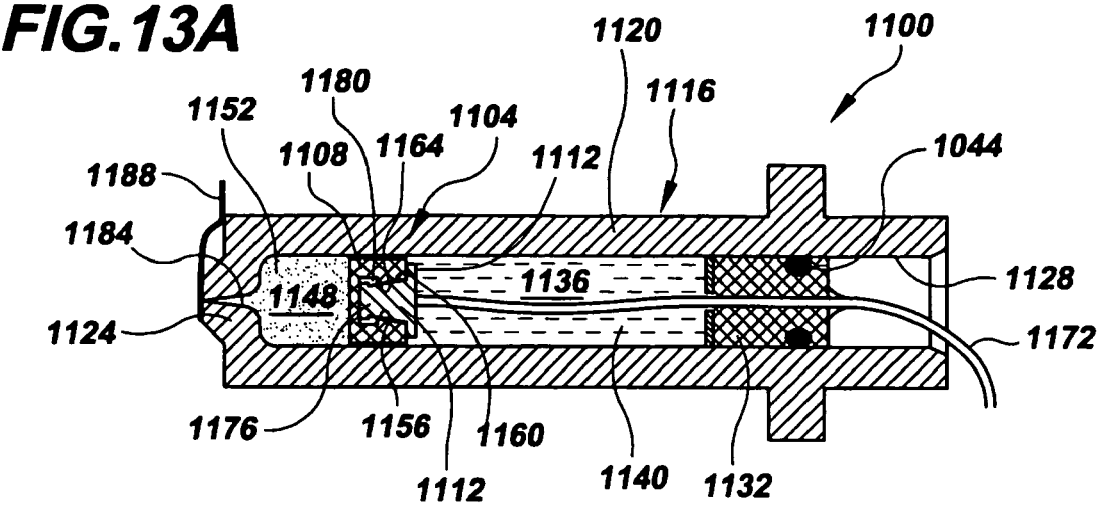
FIGS. 13A-13D are cross-sectional views of an inline-reservoir cartridge of the present invention having an expandable plug valve, illustrating its operation.
Figure 13B:
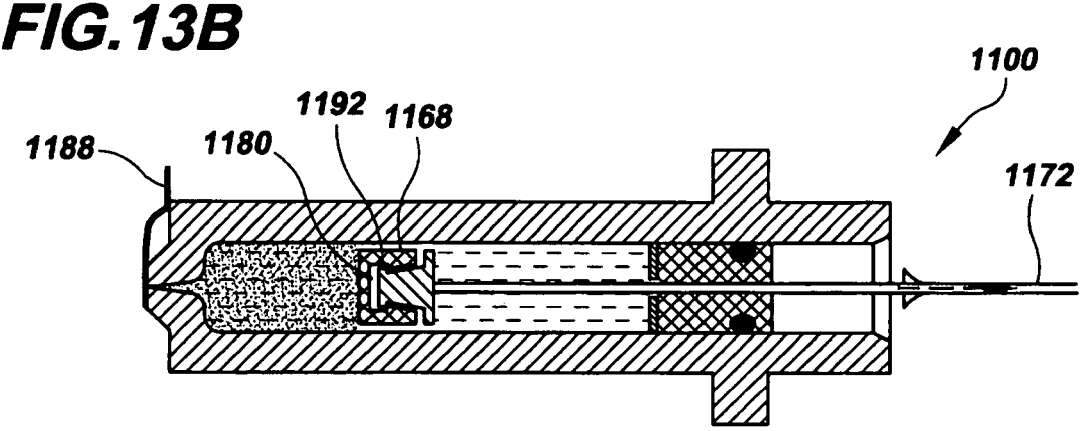
Figure 13C:
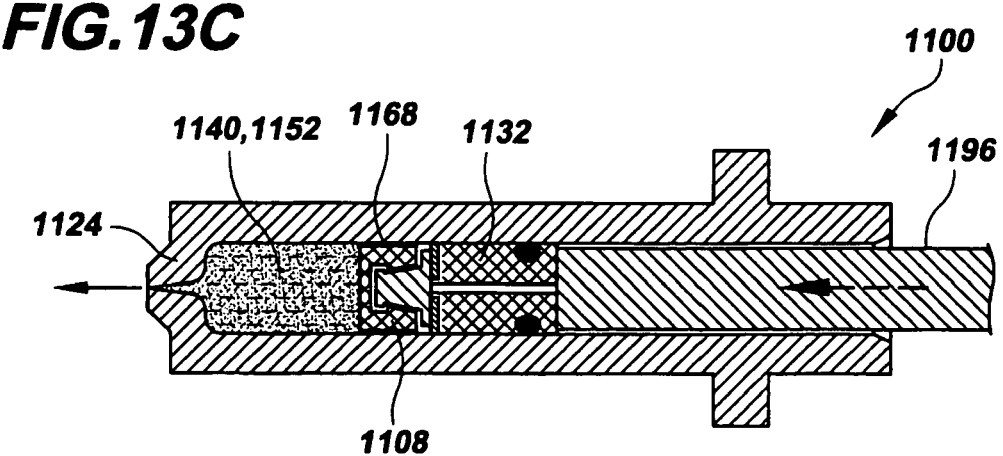

Valve 1104 may be actuated by a valve actuator 1172 attached to movable wedge 1112. Valve actuator 1172 may be the same as or similar to valve actuator 756 described above in connection with FIGS. 9A-9D. Each of expandable plug 1108 and movable wedge 1112 may be complementarily configured to allow the expandable plug to move with the movable wedge when valve 1104 is open and being moved by valve actuator 1172. For example, movable wedge 1112 may be provided with a head 1176 contained in a complementarily-sized receiver 1180 within expandable plug 1108 that prevents the movable wedge from entirely disengaging the expandable plug. Keeping expandable plug 1108 engaged with movable plug 1112 during retraction of valve 1104 promotes mixing by creating disturbances in fluid 1140 as the expandable plug moves and forces the fluid to flow in passageway 1168 (FIGS. 13B and 13C).

Cartridge 1100 may further include an outlet 1184 for passing liquid 1140 or the liquid mixed with material 1152, if provided, out of the cartridge during ejection. Outlet 1184 may be located, e.g., in end wall 1124, and may be of any suitable type, such as a high-pressure nozzle, a low-pressure nozzle or a passageway in fluid communication with another member, such as a hypodermic needles or tube, among others. Outlet 1184 may be sealed with a suitable outlet seal, such as peel-away seal 1188 shown, cap, plug or frangible seal, among others.

Cartridge 1100 may be used as follows. With continuing reference to FIG. 13A, FIG. 13A illustrates an initial state of cartridge 1100, wherein fluid 1140 is contained in first chamber 1136, material 1152 is contained in second chamber 1148, valve 1104 is located immediately adjacent the material, movable wedge 1112 is expanding expandable plug 1108 into sealing engagement with sidewall 1120 of housing 1116 and peel-away seal 1188 is sealing outlet 1184. To initiate mixing of fluid 1140 with material 1152, valve actuator 1172 is retracted within cavity 1156 so as to move movable wedge 1112 in a direction away from end wall 1124 out of wedging engagement with expandable plug 1108, as shown in FIG. 13B. Valve actuator 1172 may be retracted manually, or using a mechanism, such as ejector 32 of FIG. 1. Once movable wedge 1112 has been moved sufficiently, expandable plug 1108 will retract to form passageway 1168, allowing fluid 1040 to pass from first chamber 1136 to second chamber 1148.

As valve actuator 1172 is continued to be retracted, head 1176 of movable wedge 1112 engages a shoulder 1192 of receiver 1180, pulling expandable plug 1108 along with the movable wedge. Retraction of valve actuator 1172 may be continued until valve 1104 contacts piston 1132. Depending upon the manner in which fluid 1140 and/or material 1152 will be ejected from cartridge 1100, valve actuator 1172, or portion thereof, may be removed so as to not interfere with the ejection process. As mentioned above, valve actuator 1172 may be provided with a stress concentrator that sufficiently stresses the actuator upon contact with piston 1132 that the actuator breaks at the stress concentrator. The broken-off portion of valve actuator 1172 may then be removed. In alternative embodiments, valve actuator 1172 may be severed using a severing device that is either integral with or separate from cartridge 1100, or may otherwise be removable.

Figure 13D:
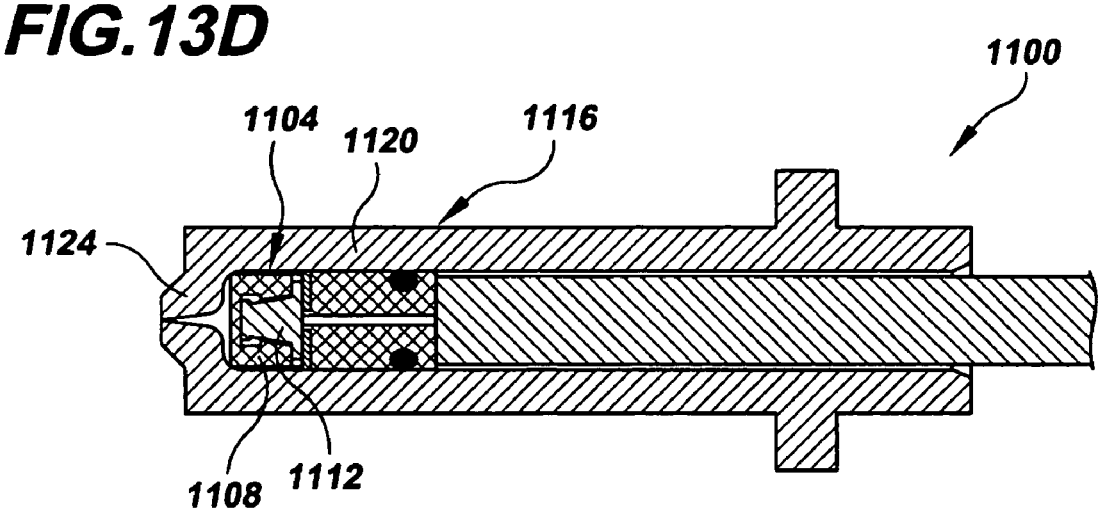

Just prior to ejection, peel-away seal 1188 may be removed to allow ejection of fluid 1140 and/or material 1152 from cartridge 1100. As shown in FIG. 13C, ejection may be effected by pushing piston 1132 toward end wall 1124, e.g., using a plunger 1196. Plunger 1196 may be separate from piston 1132 as shown or integral with the piston in a manner similar to piston 76 and plunger 60 described above relative to cartridge 52 of FIG. 2A, among others. If plunger 1196 is separate from piston 1132, it may be part of an ejector 32, e.g., ejector of FIG. 1. If plunger 1196 is integral with piston 1132, valve actuator 1172 (see FIGS. 13A and 13B) may extend at least partway through the plunger to allow for removing removable valve member 1112. As piston 1132 is continued to be pushed toward end wall 1124, it contacts and then pushes expandable plug 1108 toward the end wall until ejection of fluid 1140 and/or material 1152 is complete or the desired amount of fluid has been ejected. When valve 1104 reaches end wall 1124, as shown in FIG. 13D, movable wedge 1112 may be driven into wedging engagement with expandable plug 1108 so as to expand the plug into snug engagement with sidewall 1120 of housing 1116, rendering cartridge 1100 unusable.

Figure 14A:
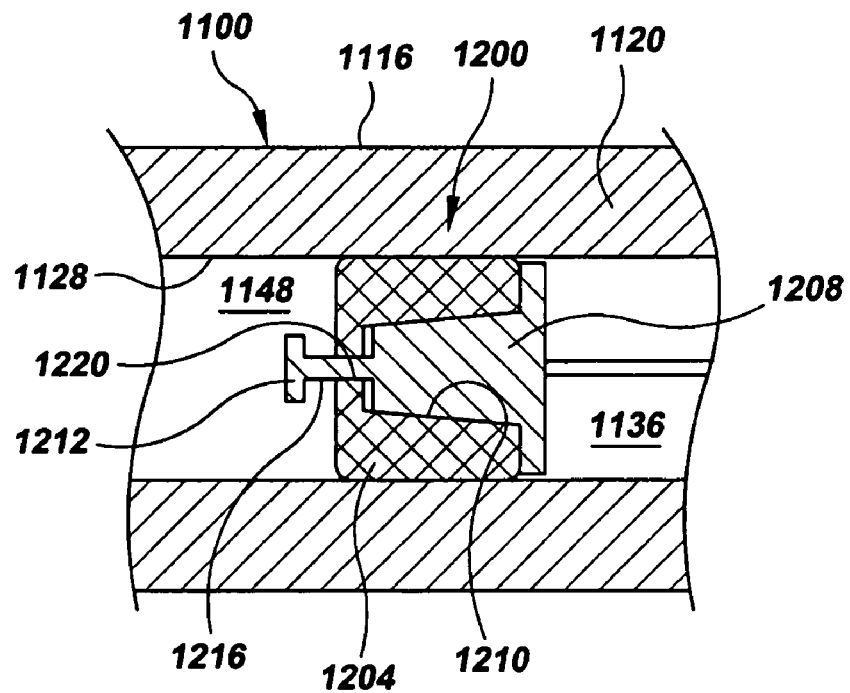
FIGS. 14A and 14B are enlarged cross-sectional partial views of an alternative expandable plug valve that may be used in place of the expandable plug valve shown in FIGS. 13A-13D.
Figure 14B:
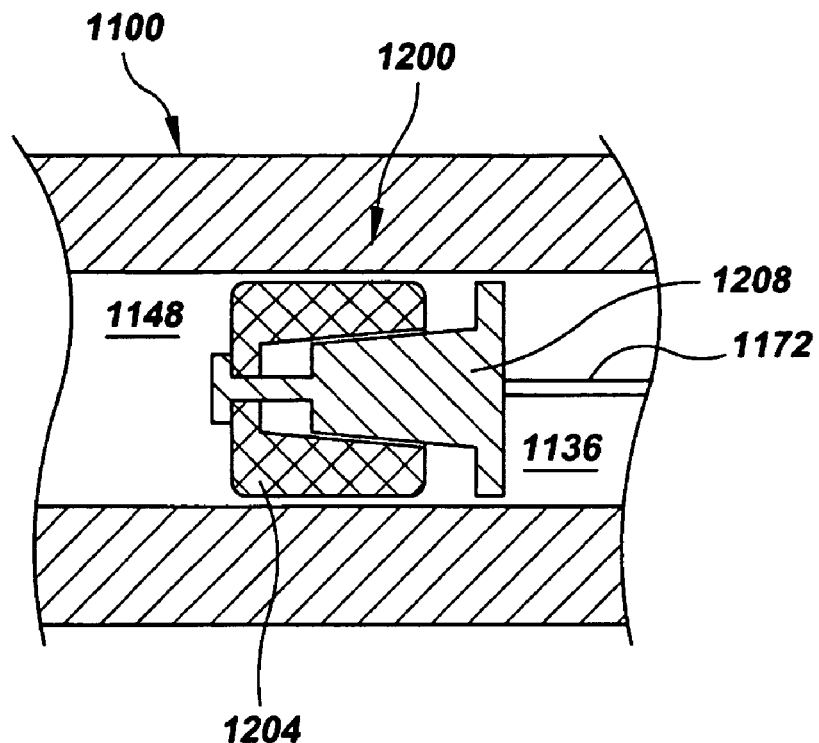

FIGS. 14A and 14B show an alternative valve 1200 comprising an expandable plug 1204 and a movable wedge 1208. Valve 1200 may be used with cartridge 1100 shown in FIGS. 13A-13D, or similar device. Valve 1200 is generally similar to valve 1104 of FIGS. 13A-13D in terms of configuration. That is, movable wedge 1208 is movable within a cavity 1210 in expandable plug 1204 so as to change states of the expandable plug between a first state (FIG. 14A), wherein the wedge expands the plug so as to press the plug into sealing engagement with sidewall 1120 of housing 1116, and a second state (FIG. 14B), wherein the wedge is moved to allow the plug to contract to a size that allows a fluid to pass between the sidewall and plug between first chamber 1136 and second chamber 1148. One difference between valve 1104 of FIGS. 13A-13D and valve 1200 of FIGS. 14A and 14B is the location of head 1212 of movable wedge 1208 relative to expandable plug 1204. In valve 1104 of FIGS. 13A-13D, head 1176 is located within receiver 1180 in expandable plug 1108; in valve 1200 of FIGS. 14A and 14B, head 1212 is located outside of expandable plug 1204. In the latter case, a neck 1216 of movable wedge 1208 extends through an opening 1220 in expandable plug 1204. However, the operation of valve 1200 of FIGS. 14A and 14B is substantially the same as the operation of valve 1104 of FIGS. 13A-13D. If desired, neck 1216 may be designed to break upon impact of head 1212 with the end wall 1124 (FIG. 13A-13D) of housing 1116 at the end of the ejection of fluid from within the cartridge, i.e., when valve 1200 is in a position similar to the position of valve 1104 as shown in FIG. 13D.

Figure 15A:
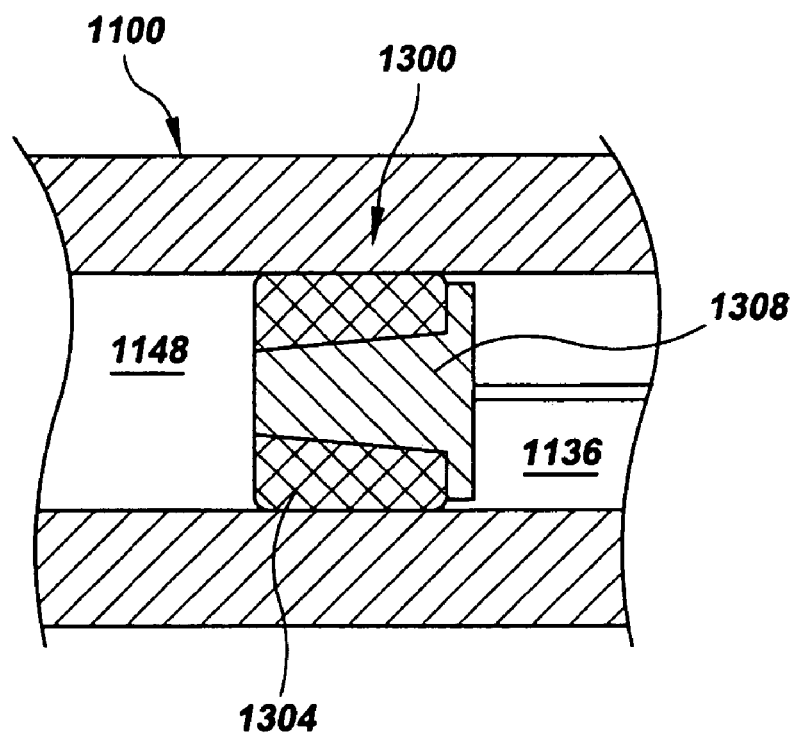
FIGS. 15A and 15B are enlarged cross-sectional partial views of another alternative expandable plug valve that may be used in place of the expandable plug valve shown in FIGS. 13A-13D.
Figure 15B:
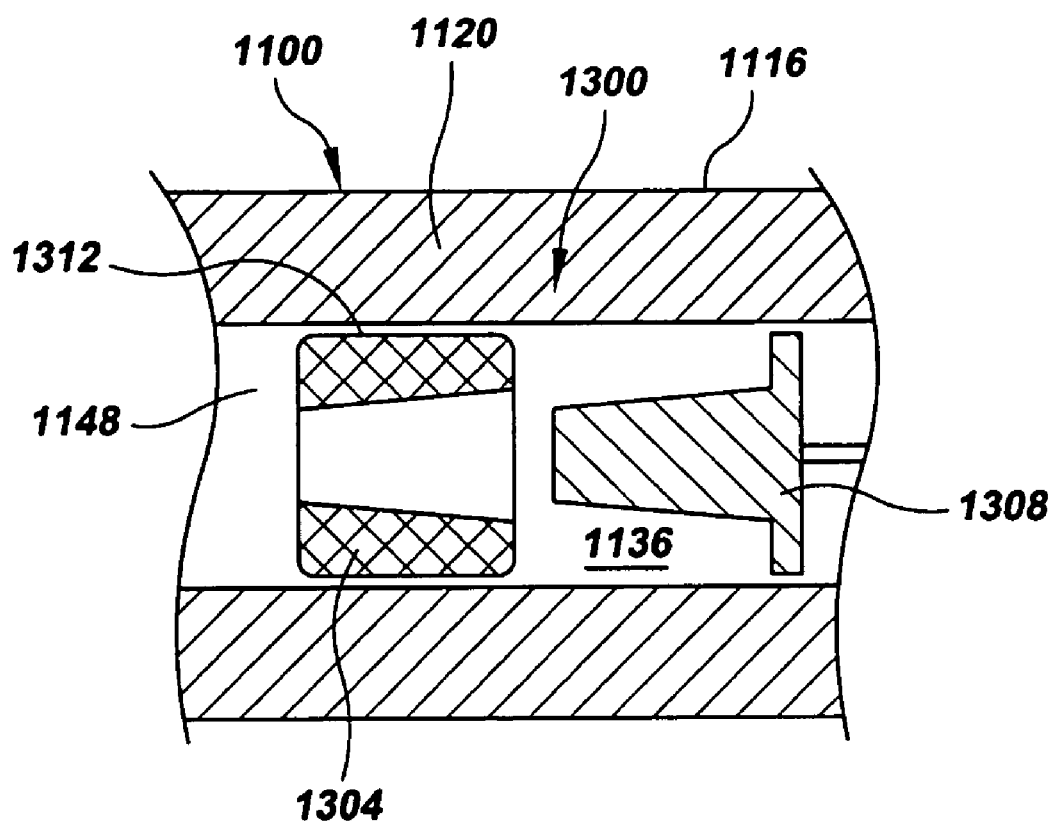

FIGS. 15A and 15B show an alternative valve 1300 comprising an expandable plug 1304 and a removable wedge 1308. Valve 1300 may be used with cartridge 1100 shown in FIGS. 13A-13D in lieu of valve 1104, or it may be used with a device similar to this cartridge. Valve 1300 of FIGS. 15A and 15B is somewhat a hybrid of valve 1004 of FIGS. 12A-12D and valve 1104 of FIGS. 13A-13D. That is, expandable plug 1304 is generally stationary when removable wedge 1308 is disengaged from the plug (similar to stationary member of FIGS. 12A-12D), but the plug contracts upon removal of the wedge (similar to movable wedge 1112 of FIGS. 13A-13D. When mixing is desired, removable wedge 1308 is disengaged from its fully-engaged position (FIG. 15A) with respect to expandable plug 1304 using, e.g., valve actuator 1172, to pull the wedge from the plug. Once removable wedge 1308 is removed, expandable plug 1304 contracts (FIG. 15B) so as to form a passageway 1312 between sidewall 1120 of housing 1116 and the plug, so as to allow a fluid to pass from first chamber 1136 to second chamber 1148. During ejection of the fluid from cartridge 1100, which generally proceeds as described above in connection with FIGS. 13A-13D), removable wedge 1308 is pushed by a piston (e.g., piston 1132 of FIG. 13A) back into engagement with expandable plug 1204, which is then pushed to the end wall (not shown) of housing 1116. At the end of ejection, removable wedge 1308 is generally firmly engaged with expandable plug 1304 so that valve 1300 is essentially stuck adjacent the end wall. This can be a beneficial feature for some applications because, at this point, cartridge 1100 may be substantially rendered unusable.

Those skilled in the art will readily appreciate that although various features of the invention have been mostly described above in terms of cartridges usable, as shown in FIG. 1, with an injector 32 and/or a fill station 28, the invention is not so limited. For example, rather than each of the above described ejection devices being cartridges, these devices may alternatively be any type of syringe, including medical syringes and syringes for delivering fluids, such as adhesives, sealants, lubricants, paints, flavorings, additives and reagents, among many others.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A syringe, comprising:
   a) a housing defining:
      i) a chamber having a first longitudinal central axis; and
      ii) a reservoir and having a second longitudinal central axis substantially collinear with said first longitudinal central axis;
   b) a valve located between said chamber and said reservoir;
   c) a piston spaced from said valve along said second longitudinal axis; and
   d) an actuator coupled to said valve so that said valve is opened by moving said actuator independently of said piston, and at least a portion of said valve is moved generally along said second longitudinal central axis by said actuator when said actuator is so moved:
   wherein said valve includes an expandable plug and a wedge when said actuator is moved, said expandable plug being in non-sealing relation with said housing when said valve is open and said wedge wedging said expandable plug into sealing engagement with said housing when said valve is closed.

2. A syringe according to claim 1, wherein the entirety of said valve is moved generally along said second longitudinal central axis by said actuator when said actuator is moved.

3. A syringe according to claim 1, wherein both said expandable plug and said wedge are moved generally along said second longitudinal central axis by said actuator when said actuator is moved.

4. A syringe according to claim 1, wherein only said wedge is moved generally along said second longitudinal central axis by said actuator when said actuator is moved.

5. A syringe according to claim 1, wherein said actuator comprises a slender elongate rod.

6. A syringe according to claim 1, wherein said actuator comprises a laterally flexible member.

7. A syringe according to claim 1, wherein said actuator includes a stress concentrator at a desired location for causing actuator to break at the stress concentrator under certain conditions.

8. A syringe according to claim 1, wherein at least a portion of said actuator is readily removable.

9. A syringe according to claim 8, wherein when said at least a portion of said actuator is removed, any remaining portion of said actuator does not extend beyond said piston.

10. A syringe according to claim 1, wherein both said expandable plug and said wedge are moved generally along said second longitudinal central axis by said actuator when said actuator is moved.

11. A syringe according to claim 1, wherein said valve is opened by moving said actuator in a withdrawing manner relative to said housing.

12. A syringe according to claim 1, wherein when a liquid is present in said reservoir and said valve is first opened, the liquid flows around said expandable plug between said housing and said expandable plug into said chamber.

13. A syringe according to claim 12, wherein said actuator is secured to said wedge and said wedge includes a tapered body and a distal head for maintaining a mechanical coupling between said wedge and said expandable plug when said valve is opened so that, when said actuator is pulled relative to said housing along said second longitudinal central axis, said expandable plug moves with said actuator and said wedge along said second longitudinal axis.

14. A syringe according to claim 13, wherein said expandable plug includes a receiver for receiving said head of said wedge with an interference fit that creates said mechanical coupling.

15. A syringe according to claim 14, wherein said receiver comprises a cavity in said expandable plug, said cavity being closed at an end proximate said chamber.

16. A syringe according to claim 13, wherein said wedge includes a neck supporting said head, said neck extending through said expandable plug so that said head is located in said chamber.

17. A syringe, comprising:
a) a housing defining:
i) an ejection chamber having a first longitudinal central axis; and
ii) a reservoir having a second longitudinal central axis substantially collinear with said first longitudinal central axis; and
b) a valve located between said ejection chamber and said reservoir, said valve including a wedge and an expandable plug that includes a receiver for receiving said wedge so as to compress said expandable plug into sealing engagement with said housing.

18. A syringe according to claim 17, wherein said wedge includes a head and a neck and said expandable plug including an aperture receiving said neck therethrough.

19. A syringe according to claim 18, wherein said expandable plug includes a receiver receiving said head so as to retain said head therein when said valve is actuated.

20. A syringe according to claim 17, wherein when a liquid is present in said reservoir and said valve is first opened, the liquid flows around said expandable plug between said housing and said expandable plug into said ejection chamber.

21. A syringe according to claim 20, further comprising an actuator secured to said wedge, wherein said wedge includes a tapered body and a distal head for maintaining a mechanical coupling between said wedge and said expandable plug when said valve is opened so that, when said actuator is pulled relative to said housing, said expandable plug moves with said actuator and said wedge.

22. A syringe according to claim 21, wherein said expandable plug includes a receiver for receiving said head of said wedge with an interference fit that creates said mechanical coupling.

23. A syringe according to claim 22, wherein said receiver comprises a cavity in said expandable plug, said cavity being closed relative to said ejection chamber.

24. A syringe according to claim 21, wherein said wedge includes a neck supporting said head, said neck extending through said expandable plug so that said head is located in said ejection chamber.

* * * * *